(12) United States Patent
Madrid et al.

(10) Patent No.: US 9,707,078 B2
(45) Date of Patent: Jul. 18, 2017

(54) EXPANSION DEVICE AND METHOD FOR TREATING VASCULAR PASSAGEWAYS

(71) Applicant: Edwards Lifesciences Corporation, Irvine, CA (US)

(72) Inventors: Gilbert Madrid, Dana Point, CA (US); Matthew T. Winston, Aliso Viejo, CA (US); Sam Sok, Santa Ana, CA (US); Michael D. Franklin, Corona, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 162 days.

(21) Appl. No.: 14/475,341

(22) Filed: Sep. 2, 2014

(65) Prior Publication Data

US 2014/0371847 A1 Dec. 18, 2014

Related U.S. Application Data

(62) Division of application No. 12/969,187, filed on Dec. 15, 2010, now abandoned.

(60) Provisional application No. 61/286,595, filed on Dec. 15, 2009.

(51) Int. Cl.
*A61F 2/24* (2006.01)
*A61M 25/10* (2013.01)
*A61B 17/22* (2006.01)

(52) U.S. Cl.
CPC .. *A61F 2/2433* (2013.01); *A61B 2017/22098* (2013.01); *A61F 2/243* (2013.01); *A61F 2/2412* (2013.01); *A61F 2/2418* (2013.01); *A61F 2/2427* (2013.01); *A61M 25/10* (2013.01); *A61M 25/1002* (2013.01); *A61M 25/1011* (2013.01)

(58) Field of Classification Search
CPC .... A61F 2/2412; A61F 2/2418; A61F 2/2427; A61F 2/243; A61F 2/2433; A61M 25/10; A61M 25/1002; A61M 25/1011
See application file for complete search history.

(56) References Cited

U.S. PATENT DOCUMENTS

| | | | |
|---|---|---|---|
| 4,744,366 A | 5/1988 | Jang | |
| 4,787,388 A | 11/1988 | Hofmann | |
| 4,878,495 A | 11/1989 | Grayzel | |
| 5,108,370 A | 4/1992 | Walinsky | |
| 5,295,995 A | 3/1994 | Kleiman | |
| 5,308,356 A | 5/1994 | Blackshear, Jr. et al. | |

(Continued)

FOREIGN PATENT DOCUMENTS

| | | |
|---|---|---|
| EP | 684855 A1 | 12/1995 |
| WO | 2010042869 A1 | 4/2010 |

OTHER PUBLICATIONS

Office Action dated Feb. 4, 2016 issued in CA Application No. 2784499.

*Primary Examiner* — Robert Lynch
(74) *Attorney, Agent, or Firm* — Klarquist Sparkman, LLP

(57) ABSTRACT

Method for delivering an expandable member to a treatment location includes an elongate shaft and an expandable member coupled to a distal end of the elongate shaft. Embodiments of the expandable member are moveable between a collapsed configuration and an expanded configuration, and have an inner expandable member and a plurality of outer expandable members that at least partially surround the inner expandable member, and are suitable for delivering prosthetic heart valves and performing vavuloplasties.

16 Claims, 23 Drawing Sheets

(56) References Cited

U.S. PATENT DOCUMENTS

| | | |
|---|---|---|
| 5,342,301 A | 8/1994 | Saab |
| 5,370,685 A | 12/1994 | Stevens |
| 5,433,706 A | 7/1995 | Abiuso |
| 5,458,575 A | 10/1995 | Wang |
| 5,501,667 A | 3/1996 | Verduin, Jr. |
| 5,505,702 A | 4/1996 | Arney |
| 5,599,306 A | 2/1997 | Klein et al. |
| 5,658,311 A | 8/1997 | Baden |
| 5,704,913 A | 1/1998 | Abele et al. |
| 5,947,924 A | 9/1999 | Liprie |
| 6,117,064 A | 9/2000 | Apple et al. |
| 6,280,412 B1 | 8/2001 | Pederson, Jr. et al. |
| 6,432,080 B2 | 8/2002 | Pederson, Jr. et al. |
| 6,966,889 B2 | 11/2005 | Saab |
| 7,084,449 B2 | 8/2006 | Cheng et al. |
| 7,163,504 B1 | 1/2007 | Chiu et al. |
| 7,275,595 B2 | 10/2007 | Tocalino et al. |
| 7,384,411 B1 | 6/2008 | Condado |
| 7,524,321 B2 | 4/2009 | Saab |
| 7,618,432 B2 | 11/2009 | Pedersen et al. |
| 7,744,620 B2 | 6/2010 | Pedersen et al. |
| 2003/0069593 A1* | 4/2003 | Tremulis ............... A61F 2/2445 606/142 |
| 2008/0021546 A1 | 1/2008 | Patz et al. |
| 2009/0030503 A1 | 1/2009 | Ho |
| 2009/0082609 A1 | 3/2009 | Condado |
| 2009/0228093 A1 | 9/2009 | Taylor et al. |
| 2010/0094209 A1 | 4/2010 | Drasler et al. |
| 2010/0228277 A1 | 9/2010 | Pedersen et al. |
| 2011/0257734 A1* | 10/2011 | Chalekian ............. A61F 2/2433 623/2.11 |

\* cited by examiner

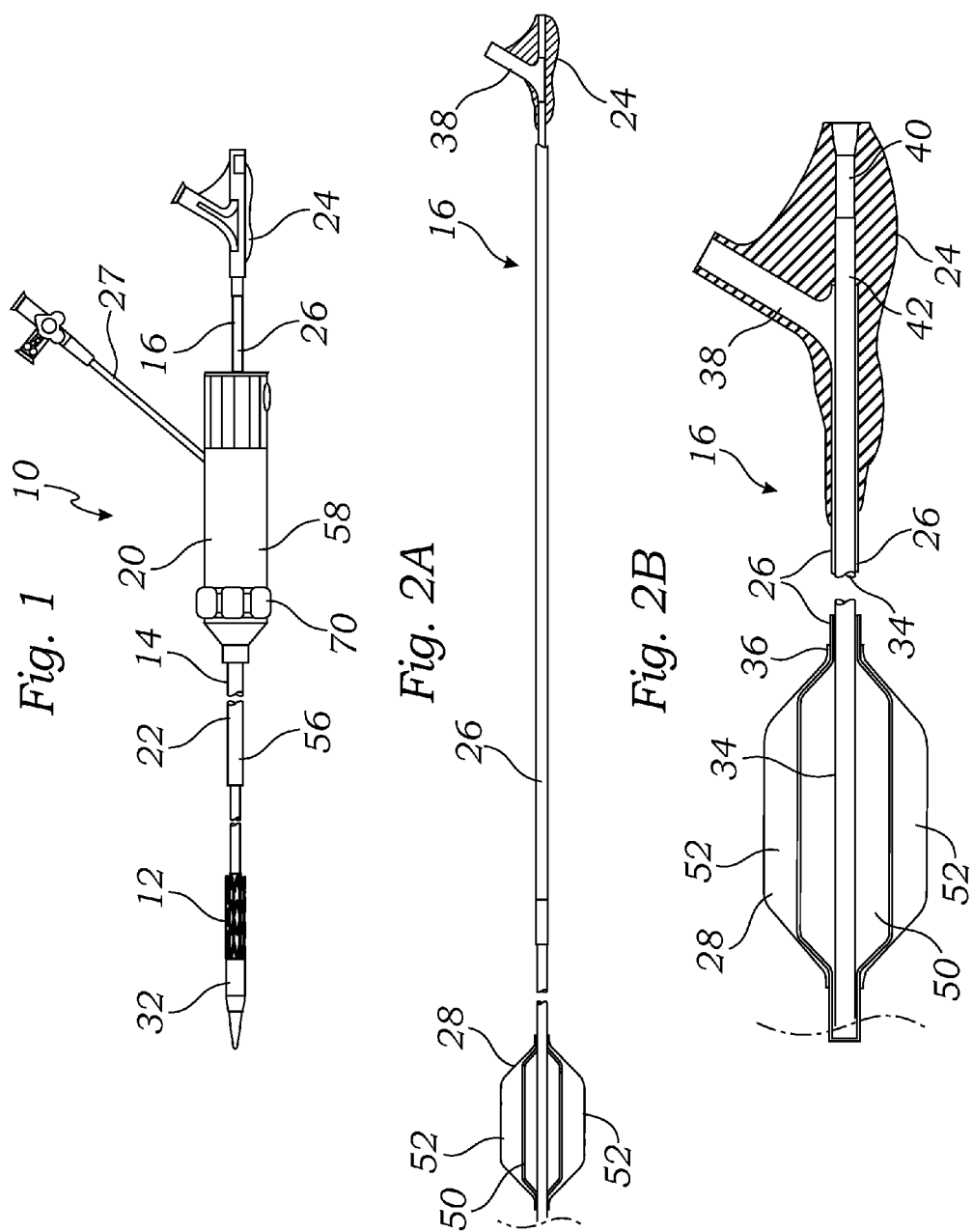

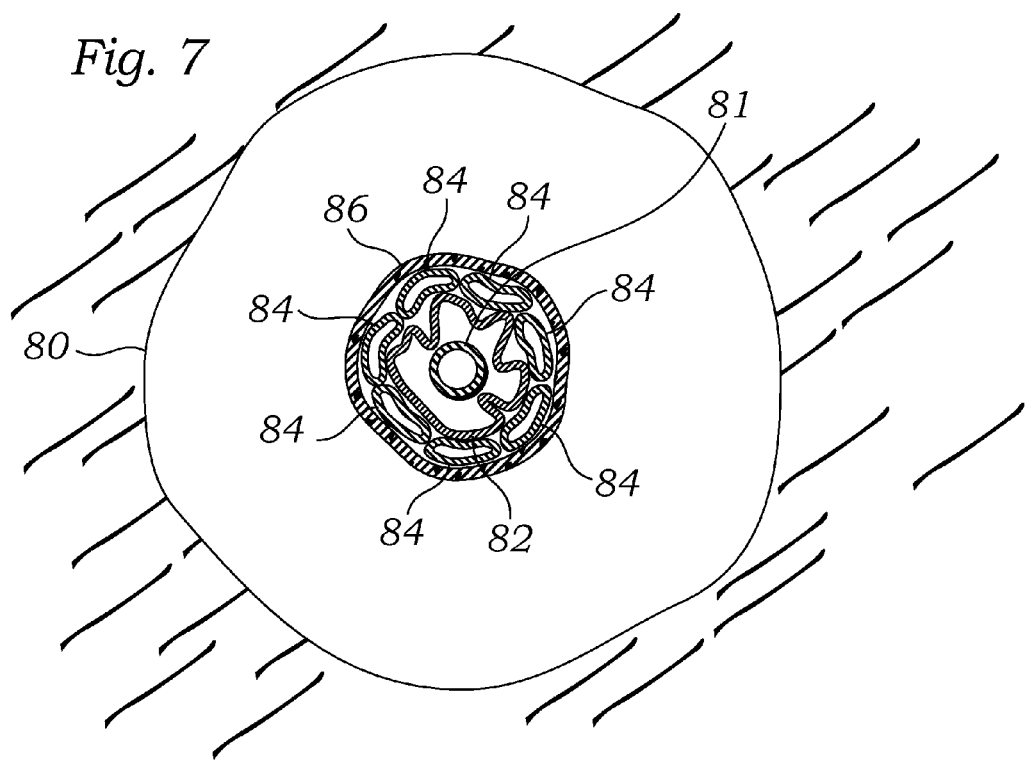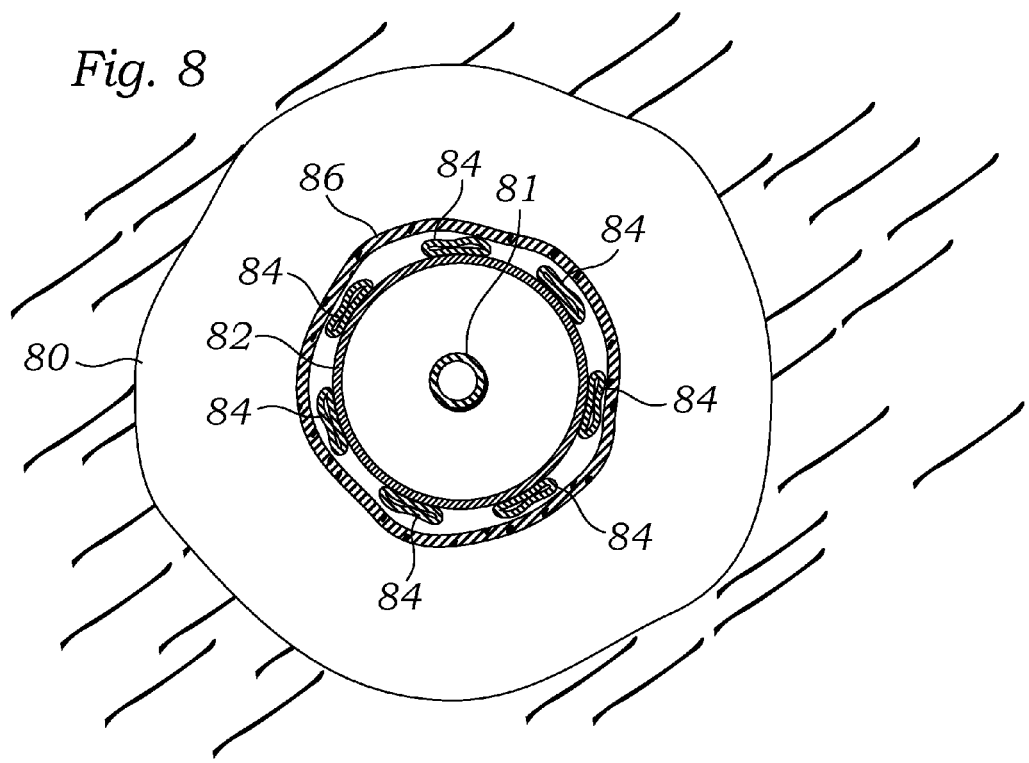

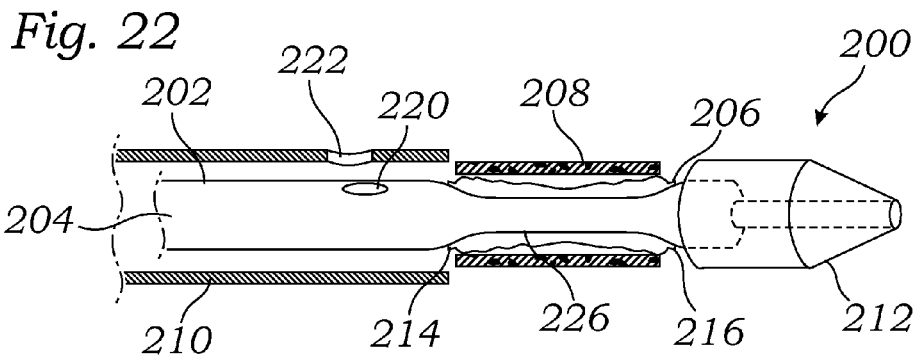
Fig. 22
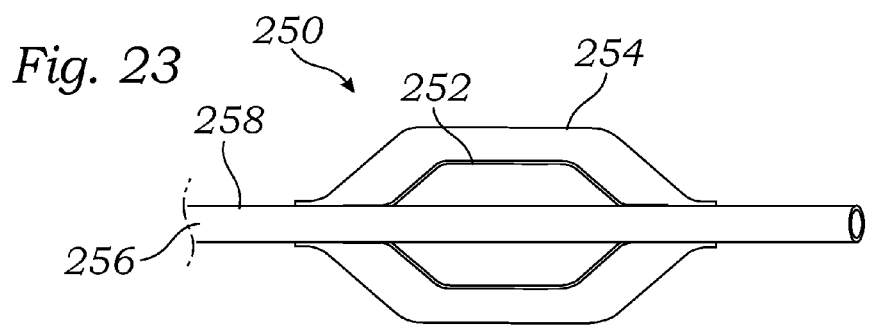
Fig. 23
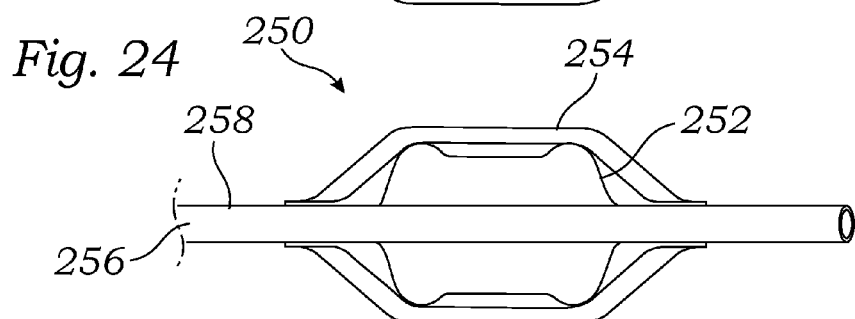
Fig. 24
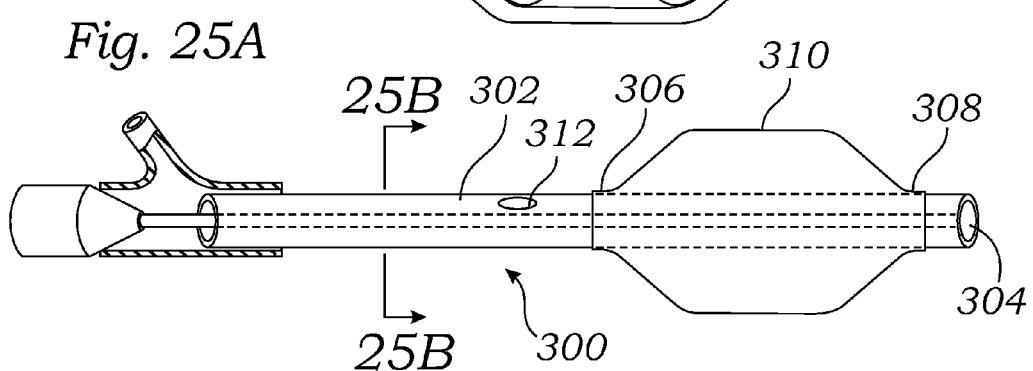
Fig. 25A
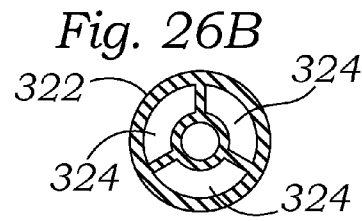
Fig. 25B
Fig. 26B

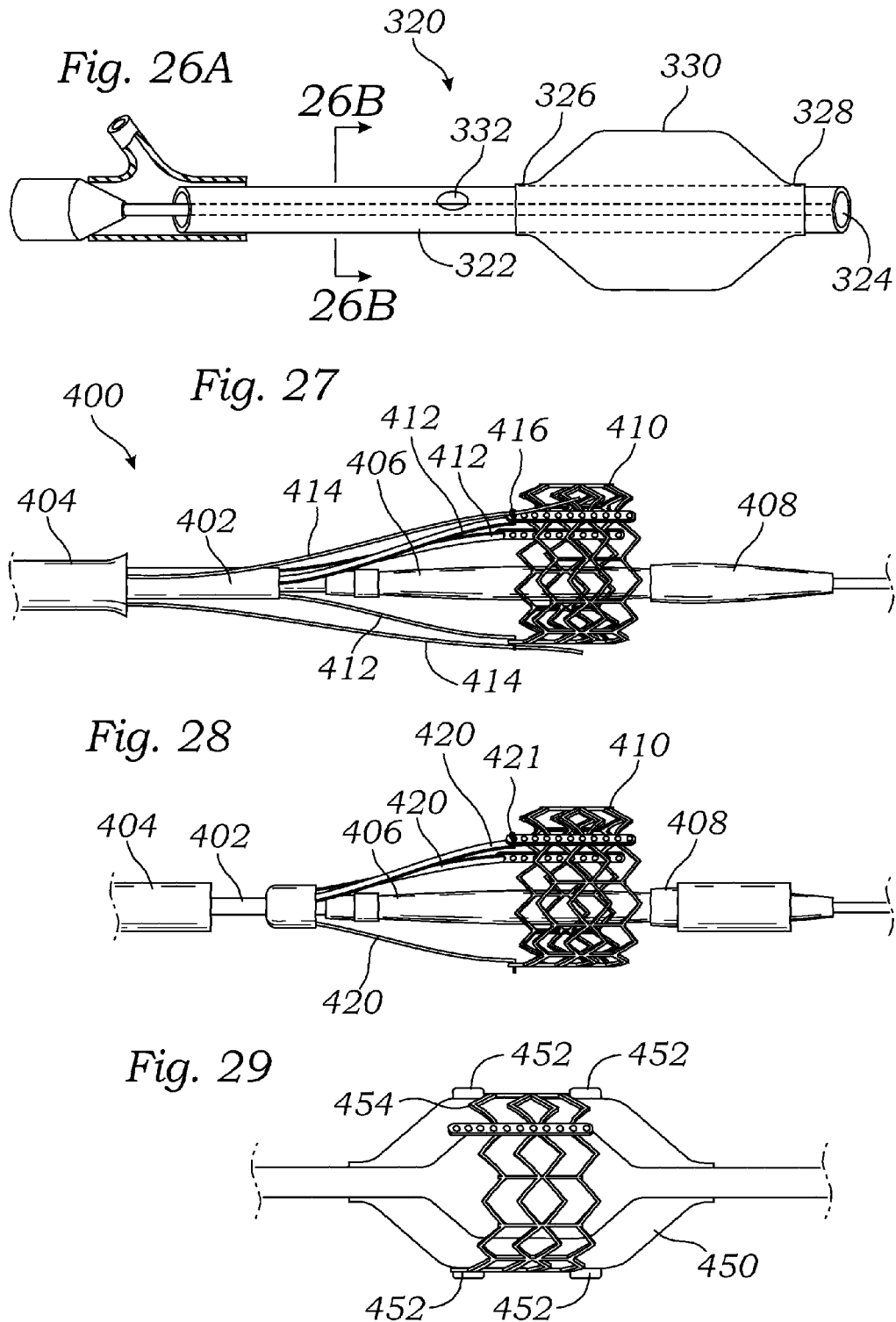

EXPANSION DEVICE AND METHOD FOR TREATING VASCULAR PASSAGEWAYS

CROSS-REFERENCE TO RELATED APPLICATION

This application is a divisional of U.S. patent application Ser. No. 12/969,187, filed Dec. 15, 2010, which claims the benefit of U.S. application Ser. No. 61/286,595, filed on Dec. 15, 2009, the entire disclosures of which are incorporated by reference herein in their entireties.

FIELD

The present disclosure is directed to apparatuses and methods that can be used in the treatment of heart valve disease, including balloon valvuloplasty and the delivery of transcatheter heart valves.

BACKGROUND

Heart valve disease is a serious problem that involves the malfunction of one or more valves of the heart. The malfunction can manifest itself in a variety of manners. For example, valve stenosis is the calcification or narrowing of a native heart valve. As a result, the native heart valve is not able to completely open and blood flow through the native valve is impeded or restricted. Another example of heart valve disease is valve insufficiency. Valve insufficiency is the failure of a native heart valve to close properly to prevent leaking, or backflow, of blood through the valve.

Various methods have been developed to treat heart valve disease. Some of these methods require a balloon member that is expanded within the native heart valve. For example, a balloon member can be used in a valvuloplasty procedure where the balloon member is positioned within the native heart valve and expanded to increase the opening size (i.e., flow area) of the native heart valve and thereby improve blood flow. Another procedure that can be performed is a valve replacement, in which a native heart valve is replaced by an artificial heart valve. The implantation of an artificial heart valve in the heart can also involve the expansion of a balloon member in the valve annulus. For example, the balloon member can be used to increase the size of the native valve prior to implantation of the artificial valve and/or it can be used to expand and deploy the artificial valve itself.

The expansion of a balloon member within a native valve or other vascular passageway, however, can temporarily block or restrict blood flow through the passageway. If blood flow is blocked or restricted in the passageway for too long, serious injury or death can occur. Furthermore, in the case of valve replacement, the positioning of the artificial heart valve may be complicated by the buildup of pressure in the left ventricle. Accordingly, valvuloplasty and valve replacement procedures, and other similar procedures which utilize expandable balloon members, must generally be performed quickly and/or with a heart pacing procedure, so that the balloon member is inflated for only a brief period.

SUMMARY

The following methods and apparatus are directed to expansion devices which allow the perfusion of blood through or around the expansion device. Certain preferred embodiments are directed to balloon members that permit perfusion of blood through or around the balloon member while a balloon member is expanded in a passageway.

During the deployment of prosthetic devices, blockage of the passageway by the balloon member during the implantation process, even for a short period of time, can introduce complications to the medical procedure. The apparatuses and methods described in various embodiments herein can reduce and/or substantially eliminate the occlusion of the passageway during expansion of a prosthetic device therein.

The apparatuses and methods described in various embodiments herein can allow for a longer prosthetic device deployment time, eliminate the need for rapid pacing of the heart and its associated risks, as well as permit repositioning of the prosthetic device during deployment.

In a first embodiment, a system for delivering an expansion device to a treatment location is provided. The system includes an elongate shaft having a distal end and an expansion device coupled to the distal end of the elongate shaft and moveable between a collapsed configuration and an expanded configuration. The expansion device has a distal end and a proximal end, and the expansion device can include an inner expandable member and a plurality of outer expandable members. The plurality of outer expandable members can at least partially surround the inner expandable member.

In specific implementations, the inner expandable member can be expanded independently of the plurality of outer expandable members. In other specific implementations, one or more of the plurality of outer expandable members can be expanded independently of the other of the plurality of outer expandable members. In other specific implementations, the plurality of outer expandable members are not fixed relative to an outer surface of the inner expandable member at an area between the proximal and distal ends of the expandable member. Alternatively, in other specific implementations, the plurality of outer expandable members can be fixed at the proximal and distal ends of the expandable member.

In other specific implementations, the inner expandable member can comprise a plurality of inner balloon members. In other specific implementations, at least some of the outer expandable members are in contact with only one inner balloon member when the expandable member is in its expanded configuration.

In other specific implementations, the inner expandable member comprises a plurality of struts that have a proximal and distal end. The proximal and distal ends of the struts can be movable from a first orientation where the proximal and distal ends of the struts are further apart to a second orientation where the proximal and distal ends of the struts are closer together. In the first orientation, the inner expandable member is in a collapsed configuration and in the second orientation the inner expandable member is in an expanded configuration.

In other specific implementations, the inner expandable member can comprise a first inner balloon and a second inner balloon member. The first inner balloon member can have a smaller expanded diameter than the second inner balloon member. The first and second inner balloon members can be substantially coaxial with one another, and the first and second inner balloon members can be expanded independently of each other.

In other specific implementations, a prosthetic device can be provided in a crimped configuration, and the outer expandable members can have an outer surface configured to engage the prosthetic device. In other specific implementations, the prosthetic device can be an artificial heart valve having a plurality of leaflets forming a plurality of commissures, and the artificial heart valve can be configured to be positioned on the outer surface of the outer expandable members in an orientation where the outer expandable members are spaced apart from one or more of the plurality of commissures of the prosthetic device.

In other specific implementations, the inner expandable member has a distal portion, a proximal portion, and an intermediate portion between the distal and proximal ends, and, when the inner expandable member is in an expanded configuration, a diameter of the intermediate portion is smaller than a diameter of the distal portion. In other specific implementations, when the expandable member is in the expanded configuration, gaps are provided between adjacent outer expandable members. In other specific implementations, the inner expandable member and outer expandable members comprise balloon members. In other specific implementations, a perfusion lumen can extend through the shaft between the distal end and the proximal end of the expandable member, thereby providing an additional pathway for blood to pass through the expandable member during use.

In another embodiment, a system for delivering an expandable member to a treatment location is provided. The delivery system comprises an elongate shaft having a distal end portion and an expandable member coupled to the distal end portion of the elongate shaft and moveable between a collapsed configuration and an expanded configuration. The expandable member can have a distal end and a proximal end, and the expandable member can include a plurality of projections extending from the surface of the expandable member. When the expandable member is in the expanded configuration, the plurality of projections can define at least one passageway between the distal end and the proximal end of the expandable member.

In other specific implementations, the expandable member can be a balloon member. In other specific implementations, the at least one passageway can include at least one longitudinal passageway and at least one circumferential passageway between the distal end and the proximal end of the expandable member. In other specific implementations, the passageway can comprise a substantially helical passageway between the distal end and the proximal end of the expandable member. In other specific implementations, the expandable member can comprise a plurality of areas that have a generally circular cross section along the length of the expandable member.

In another embodiment, an apparatus for delivering a prosthetic valve through the vasculature of a patient is provided. The apparatus includes a main catheter comprising an elongated shaft and a balloon catheter having an elongated shaft with at least one opening extending through a side surface of the shaft and a balloon member connected to a distal end portion of the shaft. The shaft of the balloon catheter can be capable of moving longitudinally within the shaft of the main catheter. The balloon catheter can include a perfusion lumen extending through at least a portion of the balloon catheter, with the lumen configured to permit blood to pass through the lumen when the balloon member is in an expanded state, the blood passing through the opening in the shaft of the balloon catheter.

In other specific implementations, at least a portion of the balloon catheter under the balloon member (e.g., in the mounting area of the prosthetic valve) can include a collapsible portion that is moveable between a collapsed state which reduces a diameter of the lumen and an expanded state that increases the diameter of the lumen. In other specific implementations, the lumen can include a plurality of separate passageways extending between a proximal end and a distal end of the balloon member.

In another embodiment, a method for delivering an expandable member through the vasculature of a patient is provided. The method can include the acts of providing an expandable member at a distal end of an elongate shaft, the expandable member having a distal end and a proximal end, the expandable member comprising an inner expandable member and a plurality of outer expandable members at least partially surrounding the inner expandable member; delivering the expandable member to a treatment site; expanding the inner expandable member in a passageway of the body of the patient; expanding the plurality of outer expandable members in the passageway; and permitting blood to pass through a plurality gaps formed between an inner surface of the passageway and the inner and outer expandable members.

In other specific implementations, the method can also include the acts of providing a prosthetic device, positioning the prosthetic device on the expandable member, and deploying the prosthetic device within the passageway by the acts of expanding the inner and outer expandable members.

In other specific implementations, the act of expanding the inner expandable member can be performed independently of the act of expanding the outer expandable members. In other specific implementations, the inner expandable member can include a first inner balloon member that has a first diameter and a second inner balloon member that has a second diameter. The first diameter can be smaller than the second diameter and the first and second balloon members can be substantially coaxial with one another. The act of expanding the inner expandable member can comprise first expanding the first inner balloon member and then expanding the second inner balloon member. In other specific implementations, the act of expanding the outer expandable members can comprise expanding one or more of the outer expandable members before expanding the other of the outer expandable members.

The foregoing and other objects, features, and advantages of the invention will become more apparent from the following detailed description, which proceeds with reference to the accompanying figures.

BRIEF DESCRIPTION OF THE DRAWINGS

FIG. 1 illustrates a delivery system with an expansion device located along a distal end portion.

FIG. 2A illustrates a partial cross-sectional view of a portion of a delivery system, shown with an expansion device in an expanded configuration.

FIG. 2B illustrates a close-up view of the delivery system of FIG. 2A.

FIG. 7 illustrates a cross-sectional view of an expansion device, shown in a collapsed state and positioned within an annulus with a prosthetic device mounted thereon.

FIG. 8 illustrates a cross-sectional view of the expansion device of FIG. 7, shown in a partially expanded state.

FIG. 9 illustrates a cross-sectional view of the expansion device of FIG. 7, shown in a fully expanded state.

FIG. 10 illustrates a cross-sectional view of the expansion device of FIG. 7, shown in an expanded state, with some outer balloon members deflated.

FIG. 22 illustrates a partial cross-sectional view of a delivery system with one or more perfusion lumens and a collapsible portion.

FIG. 23 illustrates a side view of an expansion device with an inner balloon member and one or more perfusion lumens.

FIG. 24 illustrates a side view of an expansion device with an inner balloon member and one or more perfusion lumens.

FIG. 25A illustrates a partial cross-sectional view of a delivery system with one or more perfusion lumens.

FIG. 25B illustrates a cross-sectional view of the delivery system of FIG. 25A taken along line 25B-25B.

FIG. 26A illustrates a partial cross-sectional view of a delivery system with one or more perfusion lumens.

FIG. 26B illustrates a cross-sectional view of the delivery system of FIG. 26A taken along line 26B-26B.

FIG. 27 illustrates a delivery system and a method and apparatus for securing a prosthetic device to a distal end of the delivery system.

FIG. 28 illustrates a delivery system and a method and apparatus for securing a prosthetic device to a distal end of the delivery system.

FIG. 29 illustrates a delivery system and a method and apparatus for securing a prosthetic device to a distal end of the delivery system.

DETAILED DESCRIPTION

The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Figure 38C:
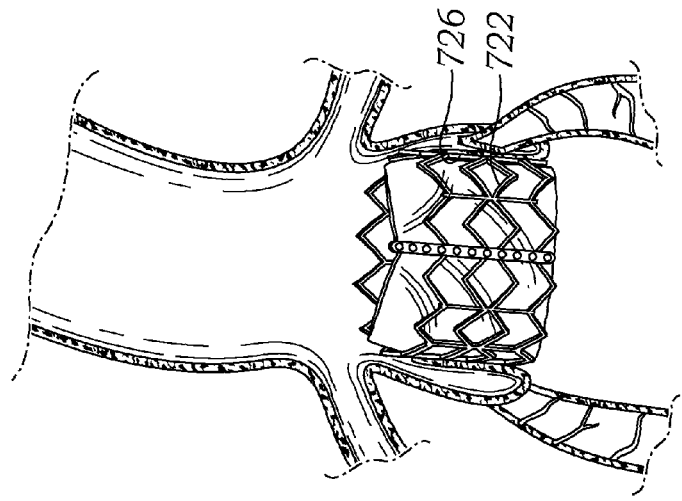
FIG. 38C illustrates the prosthetic device of FIG. 38A in a deployed state within the native aortic valve annulus.
Figure 38B:
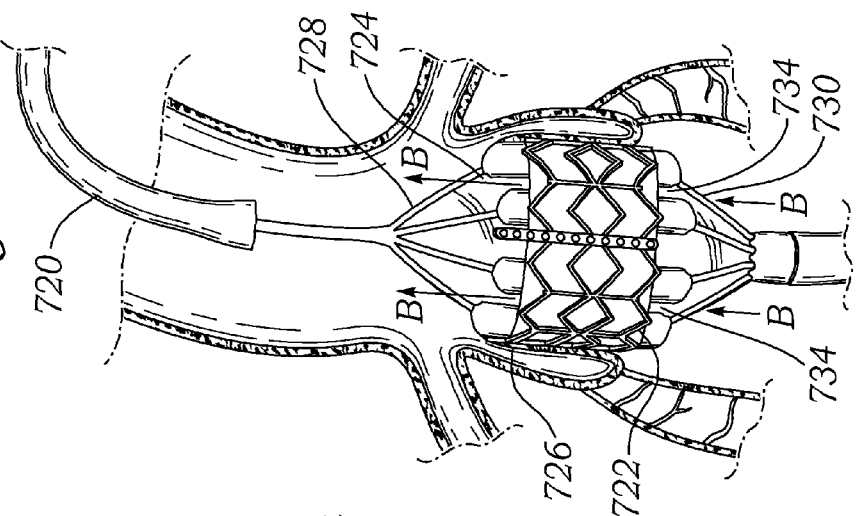
FIG. 38B illustrates a method of deploying the prosthetic device of FIG. 38A within the native aortic valve annulus using the expansion device of FIG. 3.
Figure 38A:
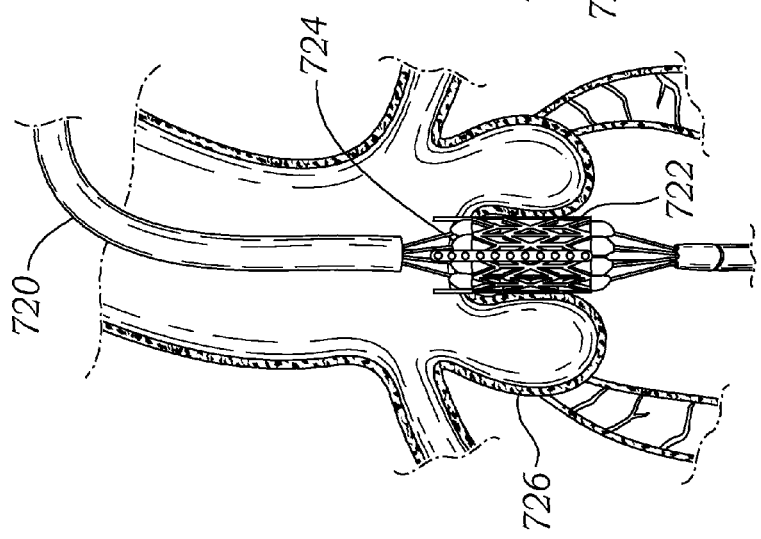
FIG. 38A illustrates a method of delivering a prosthetic device in a collapsed configuration to a treatment location within a native aortic valve annulus.

FIG. 1 shows a delivery apparatus 10 adapted to deliver a prosthetic heart valve 12 (e.g., a prosthetic aortic valve) to a heart. Apparatus 10 generally includes a steerable guide catheter 14, and a balloon catheter 16 extending through the guide catheter 14. Balloon catheter 16 can comprise multiple lumens to independently deliver fluid to one or more regions of an expansion device, as described in more detail below. The guide catheter can also be referred to as a flex catheter or a main catheter. As shown in FIGS. 38A-38C and described in more detail below, prosthetic valve 12 can be configured for deployment within an aortic annulus of a patient.

Guide catheter 14 can include a handle portion 20 and an elongated guide tube, or shaft, 22 extending from handle portion 20. Balloon catheter 16 can include a proximal portion 24 adjacent handle portion 20 and an elongated shaft 26 that extends from proximal portion 24 and through handle portion 20 and guide tube 22. Handle portion 20 can include a side arm 27 having an internal passage which fluidly communicates with the one or more lumens defined by the handle portion 20. An expansion device 28 (e.g., a plurality of inflatable balloons) can be mounted at the distal end of balloon catheter 16. In FIG. 1, prosthetic valve 12 is mounted on the expansion device 28 and is shown in a crimped state, providing prosthetic valve 12 with a reduced diameter for delivery to the heart via the patient's vasculature. It should be understood that expansion device 28 can be configured for delivery to a treatment location without a prosthetic heart valve mounted thereon, either for off-expansion device delivery of the prosthetic valve to a treatment location (as discussed below) or for use of the expansion device in a valvuloplasty procedure.

Although the illustrated embodiments discussed herein refer to the prosthetic heart valve as being crimped or mounted on the expansion device for delivery to the treatment location, it should be understood that the prosthetic heart valve can be crimped or mounted at a location different from the location of expansion device (e.g., distal or proximal to expansion device) and repositioned over the expansion device at some time before expanding the expansion device and deploying the prosthetic valve. This off-expansion device/off-balloon delivery allows the prosthetic valve to be crimped to a lower profile than would be possible if the prosthetic valve was crimped on top of the expansion device. The lower profile permits the physician to more easily navigate the delivery apparatus (including the crimped prosthetic valve) through a patient's vasculature to the treatment location. The lower profile of the crimped prosthetic valve can be particularly helpful when navigating through portions of the patient's vasculature which are particularly narrow, such as the iliac artery.

A nose piece 32 can be mounted at the distal end of the delivery apparatus 10 to facilitate advancement of the delivery apparatus 10 through the patient's vasculature to the implantation site. In some instances, it may be useful to have nose piece 32 connected to a separate elongated shaft so that nose piece 32 can move independently of other elements of delivery apparatus 10.

Nose piece 32 can be formed of a variety of materials, including various plastic materials. Alternatively, nose piece 32 can comprise an inflatable balloon member. When inflated, nose piece 32 can generally form a cone shape, such as is shown in FIG. 1. The inflation of nose piece 32, when nose piece 32 comprises a balloon member, can be achieved by having a lumen extend from a proximal end of the delivery apparatus to nose piece 32. A fluid pressurizing device can be in fluid contact with the lumen, and nose piece 32 can be inflated and deflated by the fluid pressurizing device. Nose piece 32 can be inflated to help track nose piece 32 through the vasculature of a patient and/or to provide a surface against which prosthetic valve 12 can abut, which can help maintain the position of prosthetic valve 12 on the delivery apparatus until deployment at the treatment site. In other embodiments, discussed in more detail below, nose piece 32 can have one or more lumens to provide blood perfusion through nose piece 32.

As shown in FIGS. 2A and 2B, in the illustrated configuration balloon catheter 16 can further include an inner shaft 34 (FIG. 2B) that extends from proximal portion 24 and extends coaxially through outer shaft 26 and expansion device 28. Expansion device 28 can be supported on a distal end portion of inner shaft 34 that extends outwardly from outer shaft 26 with a proximal end portion 36 of the expansion device secured to the distal end of outer shaft 26 (e.g., with a suitable adhesive). The outer diameter of inner shaft 34 is sized such that an annular space is defined between the inner and outer shafts along the entire length of the outer shaft. Proximal portion 24 of the balloon catheter can be formed with a fluid passageway 38 that is fluidly connectable to a fluid source (e.g., a saline source) for inflating the expansion device. Fluid passageway 38 is in fluid communication with the annular space between inner shaft 34 and outer shaft 26 such that fluid from the fluid source can flow through fluid passageway 38, through the space between the shafts, and into expansion device 28 to inflate the same and deploy prosthetic valve 12.

Proximal portion 24 also defines an inner lumen 40 that is in communication with a lumen 42 of inner shaft 34. The lumens 40, 42 in the illustrated embodiment can be sized to receive the shaft of a nose catheter, if desired. Inner shaft 34 and outer shaft 26 of the balloon catheter 16 can be formed from any of various suitable materials, such as nylon, braided stainless steel wires, or a polyether block amide (commercially available as Pebax®). Shafts 26, 34 can have longitudinal sections formed from different materials in order to vary the flexibility of the shafts along their lengths. Inner shaft 34 can have an inner liner or layer formed of Teflon® to minimize sliding friction with a nose catheter shaft.

Expansion device 28 can comprise a plurality of balloon members, including, for example, an inner balloon member 50 and a plurality of outer balloon members 52, as shown in FIGS. 2A and 2B. As shown more clearly in FIGS. 3 and 4, the plurality of outer balloon members 52 desirably at least partially surround inner balloon member 50. The outer balloon members 52 can be angularly spaced at substantially equal intervals around the outer surface of the inner balloon member 50, as shown.

Each outer balloon member 52 also preferably extends axially along an outer surface 54 of inner balloon member 50. Outer balloon members 52 can comprise a main outer surface 53 that is configured to receive and urge against a prosthetic valve (i.e., to radially expand the prosthetic heart valve) and/or configured to urge against an inner surface of a passageway (i.e., during a valvuloplasty procedure). In addition, each outer balloon member 52 can comprise one or more narrowed sections 55 located distal and/or proximal to the main outer surface 53.

Figure 3:
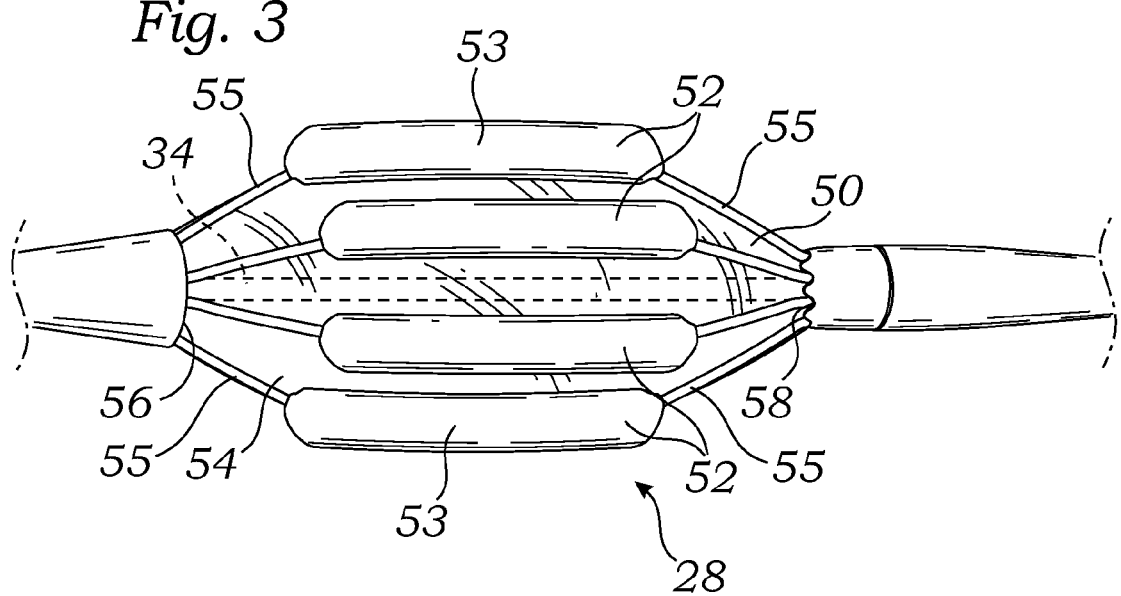
FIG. 3 illustrates a view of an expansion device of a delivery system, shown in an expanded configuration.

As best seen in FIG. 3, outer balloon members 52 are preferably fixed at a proximal end 56 and at the distal end 58 of the inner balloon member 50. The proximal and distal ends 56, 58 of outer balloon members 52 can be fixed to the inner balloon member, the outer shaft 26, or other structure near the proximal and distal ends 56, 58. If the outer balloon members 52 comprise narrowed sections 55, a portion of the narrowed sections 55 that is closest to the proximal and distal ends 56, 58 can be the portion of the outer balloon member that is fixed to the inner balloon member, the outer shaft or the other related structure.

Outer balloon members 52 can also be fixed to the outer surface 54 of inner balloon member 50 at positions intermediate to the proximal or distal ends 56, 58; however, each outer balloon member 52 is desirably fixed only at the proximal and distal ends 56, 58 so that a portion of outer balloon members 52 between the proximal and distal ends 56, 58 can freely move relative to the outer surface 54 of the inner balloon member 50. By not fixing the outer balloon members 52 to the outer surface 54 of inner balloon member 50, outer balloon members 52 can freely move along the outer surface 54. This freedom of movement allows the outer balloon members 52 to achieve a lower profile when compressed because they are able to self-align and/or move into gaps in the compressed profile of expansion device 28.

Figure 4:
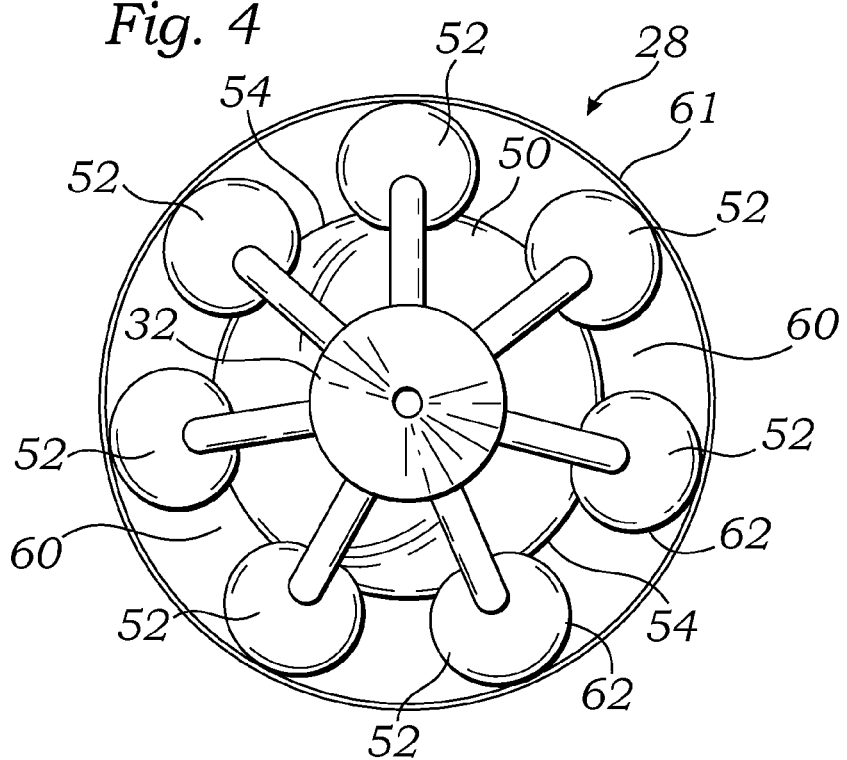
FIG. 4 illustrates an end view of an expansion device of a delivery system, shown in an expanded configuration within an annulus.

As shown in FIG. 4, when expansion device 28 is inflated (expanded) in an annulus 61 (or other similar orifice or passageway in the body), one or more gaps 60 are preferably provided between at least two adjacent outer balloon members 52. Preferably, each outer balloon member 52 is spaced apart from an adjacent outer balloon members 52 so that a side (outer) surface 62 of a first outer balloon member 52 does not contact a facing side surface 62 of an adjacent outer balloon member 52. Thus, one or more gaps 60 can permit blood perfusion through the body passageway between the distal and proximal ends 56, 58 of expansion device 28 when expansion device 28 in an expanded configuration.

It should be understood that the number and size of outer balloon members 52 can vary. For example, if the final desired expanded inner diameter of a prosthetic device is about 23 mm, the expanded diameter of the expansion device can be configured in a variety of ways to achieve this expansion. For example, inner balloon member 50 can have an expanded diameter of about 15 mm and seven outer balloon members (FIG. 4) can have an expanded diameter of about 4 mm each. Thus, the final expanded diameter of the expansion device is about 23 mm—the same diameter as the desired inner diameter of the expanded prosthetic device. In another example, inner balloon member 50 can have an expanded diameter that is about 17 mm. If the prosthetic device should be expanded to about 23 mm (as described in the previous example), the expanded diameters of outer balloon members 52 should be smaller than in the previous example. In this case, for example, the expanded diameters of outer balloon members 52 can be about 3 mm to achieve the same diameter of expansion as in the previous example (i.e., 23 mm)

In some embodiments, there are at least five outer balloon members. By providing at least five outer balloon members, the outer profile of the expansion device can approximate a circle in cross section. More preferably, there are at least seven outer balloon members as shown in FIG. 4 to provide a rounder cross-sectional profile with the outer profile of the expansion device. As described in more detail below, it can be particularly desirable to approximate a circular cross section when expanding a prosthetic heart valve using the expansion devices disclosed herein.

Figure 5A:
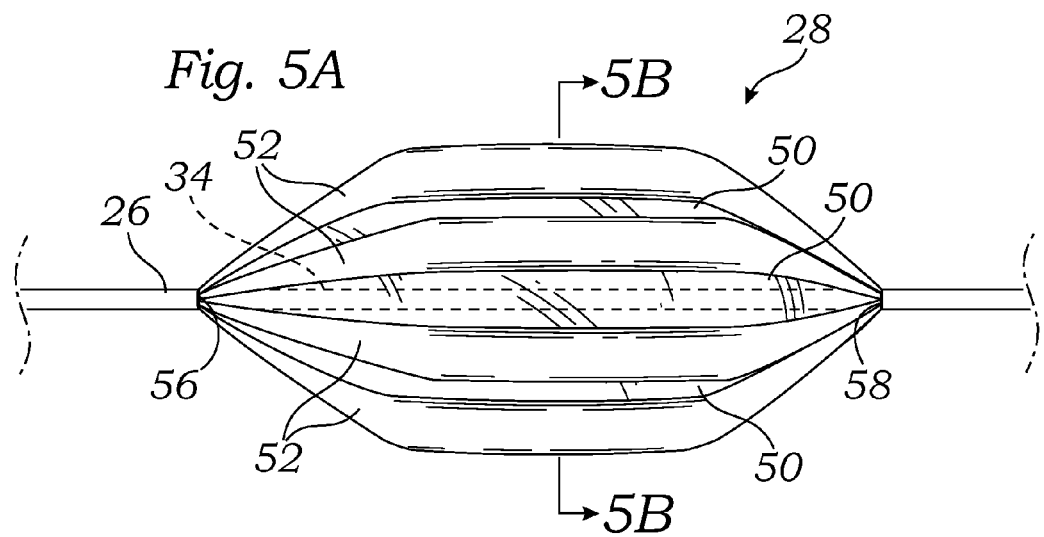
FIG. 5A illustrates a view of an expansion device of a delivery system, shown in an expanded configuration.
Figure 5B:
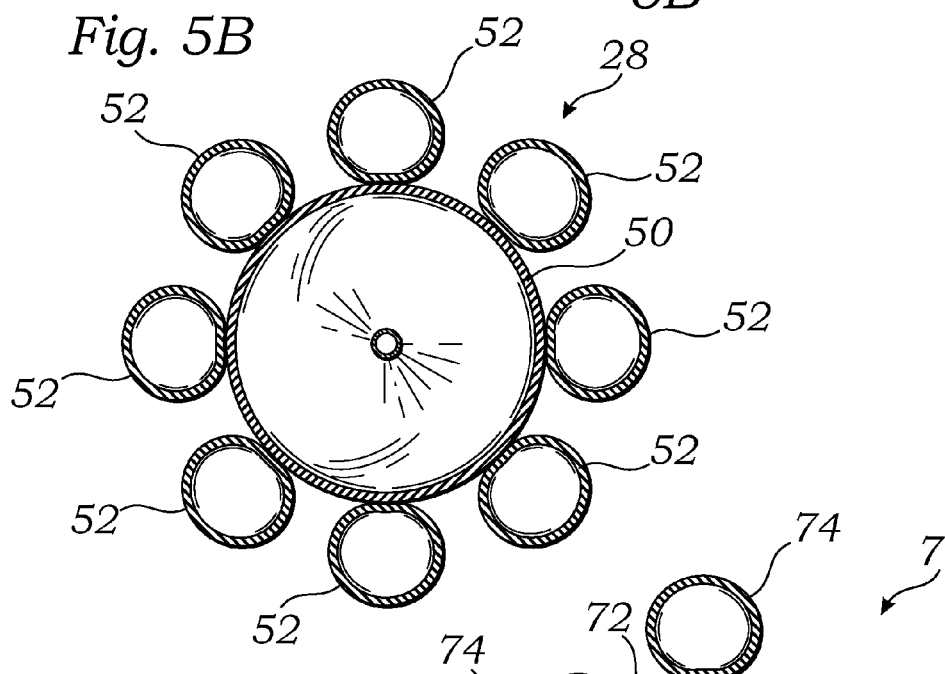
FIG. 5B illustrates a cross-sectional view taken along line 5B-5B of FIG. 5A.

FIG. 5A illustrates another embodiment of an expansion device 28 comprising an inner balloon member 50 and a plurality of outer balloon members 52. FIG. 5B illustrates a cross-sectional view of the expansion device 28, which shows that this embodiment includes eight outer balloon members 52. As discussed above, the outer balloon members 52 are preferably not fixed to the inner balloon member 50 between the proximal end 56 and distal end 58 of the expansion device 28. Each outer balloon member 52 can be secured at its respective proximal or distal ends to the proximal and distal ends respectively of the inner balloon member. If desired, outer balloon members 52 can taper to a smaller diameter (as shown in FIG. 5A) or have narrowed sections (as shown in FIG. 3) at the proximal and distal ends 56, 58.

Figure 6:
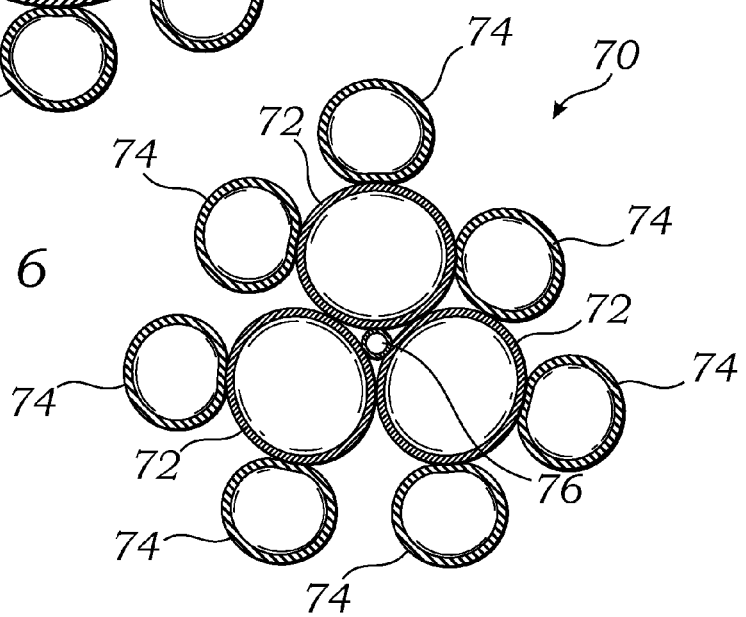
FIG. 6 illustrates a cross-sectional view of an alternative expansion device of a delivery system.

Referring to FIG. 6, a cross-sectional view of another embodiment is provided. In the embodiment shown in FIG. 6, an expansion device 70 comprises a plurality of inner balloon members 72 and a plurality of outer balloon members 74. A shaft 76 of the balloon catheter can extend through the expansion device between inner balloon members 72.

Multiple inner balloon members 72 can be used to create a balloon assembly that is capable of achieving various shapes. For example, three inner balloon members 72 can be used to create an expanded shape that is generally tri-lobular in cross section (as shown in FIG. 6). A tri-lobular shape can be useful, for example, when expanding prosthetic valves into portions of the aortic valve and/or aortic root. Alternatively, the inner balloon members and outer balloon members can be selected so that the expanded shape of the expansion device is substantially circular in cross section, as in the embodiments described above. Of course, if desired, in the embodiments described above with a single inner balloon member, the sizes (i.e., expanded diameters) of the outer balloon members can be varied to form a cross section that is a shape other than circular (e.g., tri-lobular, oval).

In each of the embodiments herein, the balloon members of an expansion device can be expanded (inflated) simultaneously or they can be inflated individually (e.g., sequentially or in one or more stages). Preferably, each inner balloon member is fluidly separate or distinct from each outer balloon member. Similarly, each outer balloon member can be fluidly separate or distinct from the other outer balloon members. By separately expanding at least some of the balloon members, the passageway in which the expansion device expands can be partially or completely occluded for a shorter period of time. For example, FIGS. 7-13 illustrate various stages of expansion of an expansion device that can be configured to expand a prosthetic device, such as a prosthetic heart valve, or to perform a valvuloplasty procedure.

As described in more detail below, in a preferred embodiment, the outer balloons can be expanded in alternating and/or sequential groups to increase blood flow between the distal end of the expansion device to the proximal end of the expansion device (and vice versa). Thus, for example, if two sequentially expandable (and deflatable) sets of outer balloon members are provided, a first set of outer balloon members can be expanded and then, after expansion of the first set, the second set of outer balloon members can be expanded. At the time the second set is expanded, the first set can be maintained in their expanded configuration. By sequentially expanding the outer balloon members in this manner, the amount of time that both sets of outer balloon members are inflated can be reduced, which is beneficial because when all outer balloon members are expanded, the perfusion paths between the ends of the expansion device are reduced. Similarly, the two sets of outer balloon members can be sequentially deflated to increase the blood perfusion paths during the procedure and reduce the amount of time in which the perfusion paths are reduced. Although this method is described with only two sets of outer balloon members, it should be understood that more than two sets of sequentially expandable and/or alternately expandable balloon members can be provided.

In addition, as described in more detail herein, the sequential and/or alternate expansion of members is not limited to outer balloon members. In various embodiments, inner and outer members (balloon or mechanical) can be sequentially expanded and/or collapsed. For example, a first inner balloon can be expanded and then one or more outer balloons can be expanded. Alternatively, the outer member(s) can be expanded and then the inner member can be expanded.

Referring to FIG. 7, an expansion device is shown in a collapsed configuration with a prosthetic device 86 crimped thereon. The expansion device comprises an inner balloon member 82 and a plurality of outer balloon members 84 in a deflated configuration and carried on an inner shaft 81. Seven outer balloon members 84 are shown, but as discussed above, in some embodiments, the number of outer balloon members can be fewer or greater. Prosthetic device 86 is crimped onto the collapsed expansion device. As discussed above, each outer balloon member 84 preferably has a portion (e.g., a central longitudinal or axial portion) that is freely floating or movable relative to the balloon member 82, which allows outer balloon members 84 to be collapsed to a lower profile shape. To deploy (expand) the prosthetic device 86, the expansion device and prosthetic device 86 can be moved to the treatment site (e.g., a body passageway or orifice) where the prosthetic device will be expanded. The treatment site can be, for example, a native valve annulus 80, as shown in FIGS. 7-8. As can be seen in FIG. 7, when the expansion device is completely collapsed with the prosthetic valve positioned thereon, blood can pass through the annulus in the space between the outer surface of the crimped prosthetic device 86 and the inner surface of the annulus 80.

Referring to FIG. 8, a first stage of deployment can comprise partially expanding the expansion device by expanding inner balloon member 82 to its expanded configuration. The expansion of inner balloon member 82 causes prosthetic device 86 to partially expand, as shown in FIG. 8. Thus, inner balloon member 82 can be expanded while outer balloon members 84 remain in their collapsed configuration. To facilitate the independent and/or separate expansion of the inner balloon member and outer balloon members, separate lumen can be provided. In some embodiments, the separate lumen can be in a side-by-side configuration; however, it should be understood that other configurations are possible.

Inner balloon member 82 preferably expands to a size sufficient to maintain a frictional force on prosthetic device 86. If desired, prosthetic device 86 can be repositioned as necessary by moving the expansion device (e.g., by moving inner shaft 81 in a proximal or distal direction). The frictional force on prosthetic device 86 can help maintain the position of the prosthetic device 86 on the expansion device.

As shown in FIG. 8, because the partially expanded expansion device and prosthetic device 86 have an outer diameter that is less that the inner diameter of the annulus, blood is still able to pass through the annulus in the space between the outer surface of the partially expanded prosthetic device 86 and the inner surface of the annulus 80.

Figures 9, 10:
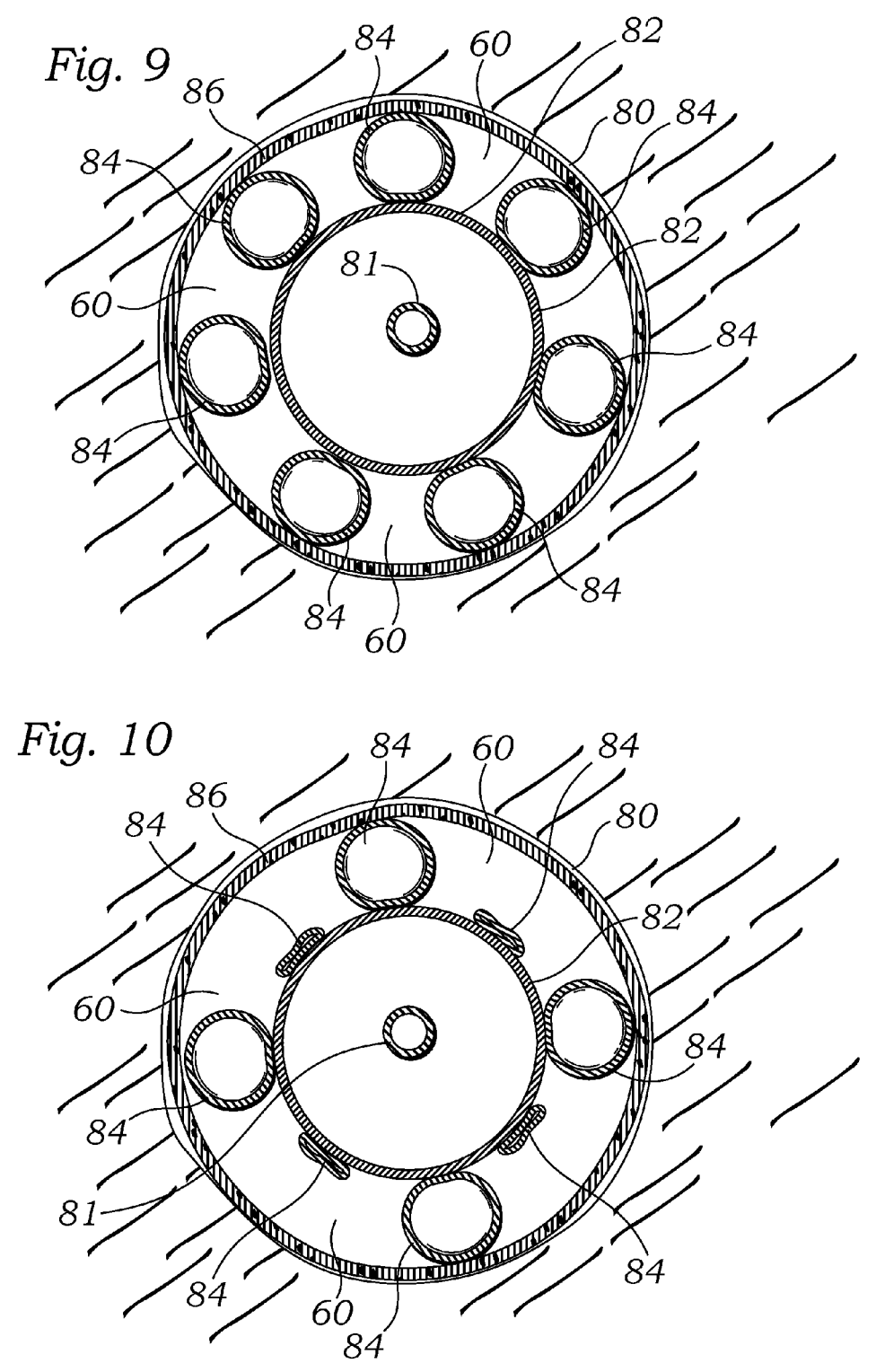

Referring to FIG. 9, the expansion device is shown in a further expanded configuration (e.g., a fully expanded configuration) with inner balloon member 82 in an expanded state and outer balloon members 84 in an expanded state. The full expansion of the expansion device also expands prosthetic device 86 to its fully deployed state. As seen in FIG. 9, and as discussed above with respect to FIG. 4, gaps 60 are present between inner balloon member 82 and outer balloon members 84, and between annulus 80 and inner balloon member 82. These gaps permit blood to pass between the proximal and distal ends of prosthetic device 86 when the expansion device is in a fully expanded condition.

Accordingly, as shown in FIGS. 7-9, the expansion device can expand a prosthetic device while permitting blood perfusion between proximal and distal ends of the expansion device. Moreover, the expansion device can be expanded in stages to maximize blood flow during deployment of a prosthetic device (or during a valvuloplasty procedure). Also, because inner balloon member 82 can be fully expanded when the prosthetic device is in a partially expanded configuration, the size and shape of the partially expanded expansion device is predictable. In contrast, although a conventional balloon member can be partially expanded during expansion of a delivery device, the shape of the conventional balloon member is generally unpredictable during expansion because balloon members do not tend to conform to predictable shapes until full expansion of the balloon member is achieved.

In some embodiments, outer balloon members 84 can be expanded before inner balloon member 82 is expanded. Preferably, when expanding outer balloon members 84 first, outer balloon members 84 can be collectively expanded to a size sufficient to maintain a frictional force on prosthetic device 86 to achieve the same repositionability as described above with respect to the embodiment where inner balloon member 82 is expanded first.

In another embodiment, outer balloon members 84 can be separately expanded relative to one another. Thus, as shown in FIG. 10, inner balloon member 82 can be expanded to partially expand the prosthetic device 86, and then outer balloon members 84 can be expanded in stages. For example, as shown in FIG. 10, alternating outer balloon members 84 are shown in an expanded state. In this manner, gaps 60 that are present between inner balloon member 82 and annulus 80 are larger than those described above in FIG. 9, and greater blood perfusion is possible through gaps 60.

The configuration shown in FIG. 10 can be illustrative of a deployment stage of a prosthetic device 86 or it can be illustrative of the collapsing of the expansion device after deployment of prosthetic device 86. That is, the deflated outer balloon members 84 shown in FIG. 10 can be in an intermediate stage and subsequently inflated to assist in the expansion of prosthetic device 86. Alternatively, the configuration shown in FIG. 10 can be illustrative of a selective collapsing (deflation) of one or more outer balloon members 84 after the prosthetic device 86 is fully deployed. Thus, the expansion device can quickly reduce its profile to allow for increased blood perfusion prior to being completely deflated or collapsed.

After expansion of the expansion device (e.g., to expand a prosthetic device or perform valvuloplasty), the expansion device can also be deflated or collapsed in stages. For example, the outer balloons can be deflated prior to deflation of the inner balloon(s). In this manner, blood can be permitted to pass between the proximal and distal ends of the expansion device in the areas adjacent to the deflated balloon members and the urgency to deflate the remaining expanded balloon members can be lessened.

Figure 11:
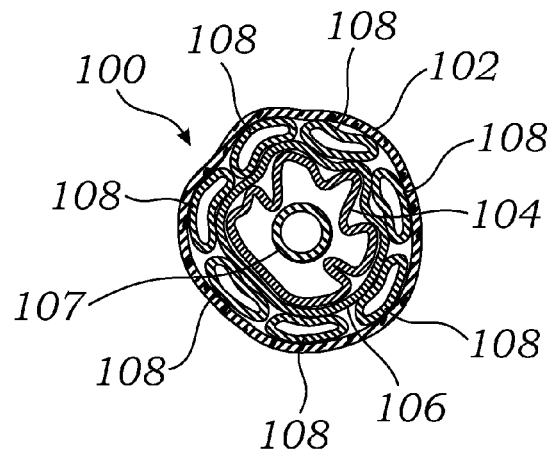
FIG. 11 illustrates a cross-sectional view of an expansion device, shown in a collapsed state and positioned within an annulus with a prosthetic device mounted thereon.

In another embodiment, an expansion device can comprise a multi-diameter inner balloon assembly comprised of a plurality of coaxially arranged inner balloon members configured such that the inner balloon members can be expanded to different diameters. For example, FIG. 11 illustrates an expansion device 100 with a prosthetic device 102 (e.g., a prosthetic valve) crimped thereon. Expansion device 100 can comprise a first inner balloon member 104 and a second inner balloon member 106. First and second inner balloon members 104, 106 are preferably coaxial. In the illustrated embodiment, first and second balloon members 104, 106 can both be carried on an inner shaft 107. In a manner similar to that described above, a plurality of outer balloon members 108 can at least partially surround the first and second inner balloon members 104, 106.

Figure 12:
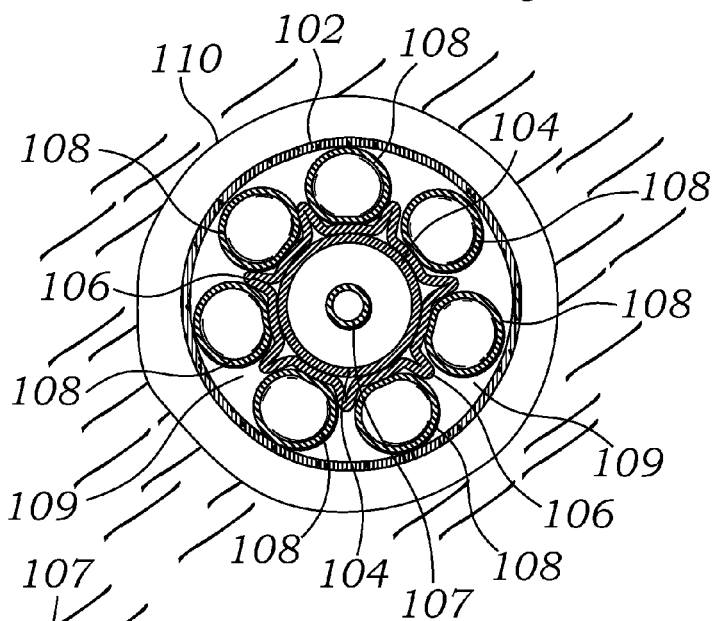
FIG. 12 illustrates a cross-sectional view of the expansion device of FIG. 11, shown in a partially expanded state.
Figure 13:
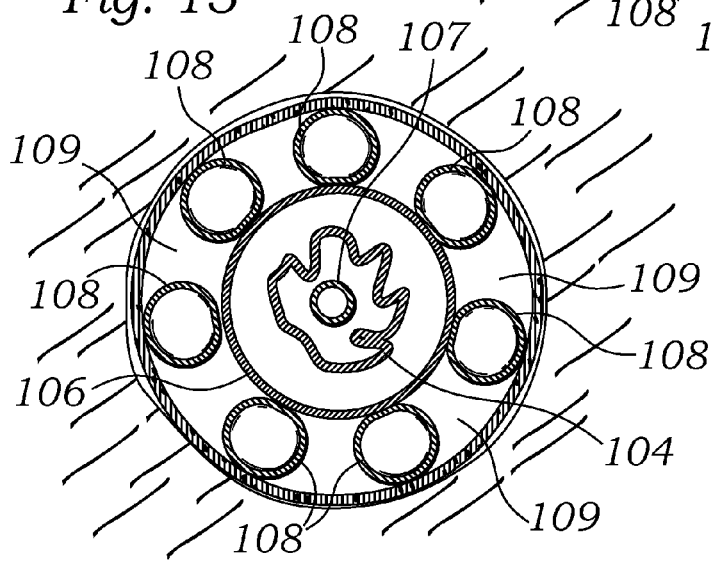
FIG. 13 illustrates a cross-sectional view of the expansion device of FIG. 11, shown in a fully expanded state.

First inner balloon member 104 and second inner balloon member 106 preferably have different diameters so that the expansion device 100 can inflate to a plurality of predictable, increasing diameters. For example, first inner balloon member 104 can have a smaller inflated diameter than second inner balloon member 106. Thus, as shown in FIG. 12, when expansion device 100 is inflated (expanded) to a first configuration, in which first inner balloon member 104 is fully inflated and outer balloon members 108 are fully inflated, the total inflated diameter (profile) of the expansion device is less than that of an inner diameter of an annulus 110. However, as shown in FIG. 13, when expansion device 100 is inflated (expanded) to a second configuration, in which second inner balloon member 106 is fully inflated and outer balloon members 108 are fully inflated, the total inflated diameter (profile) of the expansion device is substantially the same as the inner diameter of the annulus 110.

Thus, the expansion device can be inflated (expanded) in stages characterized by predictable, increasing diameters. That is, the expansion of the expansion device can include an intermediate stage (FIG. 12) between the deflated stage (FIG. 11) and the fully expanded stage (FIG. 13). As shown in FIG. 12, in this intermediate stage the expansion device 100 is only partially expanded and blood can more easily pass between the proximal and distal ends of expansion device 100. Preferably, first and second inner balloon members are concentric and coaxial so that they can expand in a predictable and uniform manner relative to the prosthetic device. In addition, as in other embodiments, it should be understood that even in the fully expanded stage (FIG. 13), blood is able to pass between proximal and distal ends of expansion device 100 by passing through the gaps (spaces) 109 present between adjacent outer balloon members 108.

As noted above, an inner member can be inflated before one or more outer members, or one or more outer members can be inflated before the inner member. By expanding the outer members first, gaps (e.g., passageways) can be formed between adjacent outer balloon members early in the expansion procedure. These gaps between adjacent outer balloons can be maintained as the inner member is expanded. In this manner, the gaps in the expansion device are present as the expansion device moves from a partially expanded state to a fully expanded state and blood can be allowed to flow across the device throughout the expansion procedure.

Figure 14:
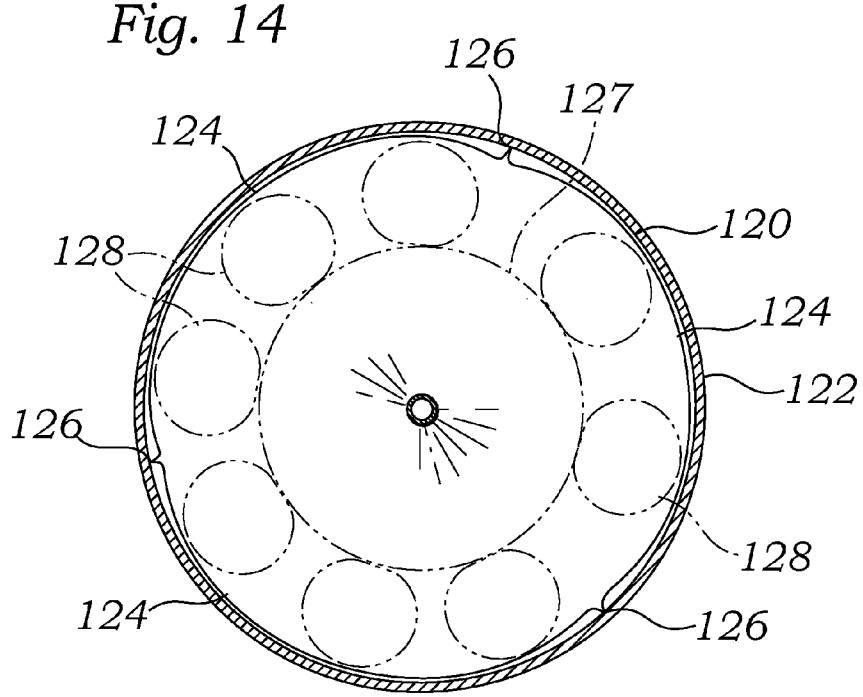
FIG. 14 illustrates a partial cross-sectional view of an expansion device with a prosthetic device mounted thereon.

In another embodiment, the expansion device can comprise an inner balloon member 127 and a plurality of outer balloon members 128 at least partially surrounding inner balloon member 127. Outer balloon members 128 can be oriented relative to a prosthetic device 120 to increase perfusion between distal and proximal ends of prosthetic device 120. For example, as shown in FIG. 14, a prosthetic device 120 can comprise a frame member 122 and a plurality of leaflets 124 coupled to frame member 122. Adjacent leaflets 124 form a plurality of commissures 126. As shown in FIG. 14, prosthetic device 120 can be mounted on the expansion device so that outer balloon members 128 are not aligned with (or spaced away from) the commissures 126. By positioning the outer balloon members 128 so that they are not located at the area of commissure 126, maximum blood perfusion between proximal and distal ends of the prosthetic device 120 can be achieved by taking advantage of blood flow through the prosthetic device 120 itself.

Although the balloon members described above can be formed in various cross-sectional shapes (e.g., round, trilobular, oval, etc.), they are preferably substantially round in cross section. When subjected to high pressure inflation, as is required to expand a prosthetic device, balloon members have a tendency to "round out," regardless of their pre-set shape. For example, although it possible to heat-set a balloon to have an oval cross section, during high pressure inflation that oval shape will tend to inflate to a substantially round, cross-sectional shape. Thus, an advantage of the embodiments described above is that each balloon member (e.g., inner and outer balloon members) can be configured to be round in cross section, yet the overall profile of the expansion device in cross section is more complex and includes gaps for blood perfusion. Therefore, even when subjected to high pressure expansion, the final shape of the expansion device is substantially the same as its preset shape since each balloon has a pre-set shape having a substantially circular cross-sectional profile. In contrast, balloon members having a non-circular cross-sectional profile may distort upon high pressure expansion and the final shape of the balloon member may not be as expected.

Figure 15:
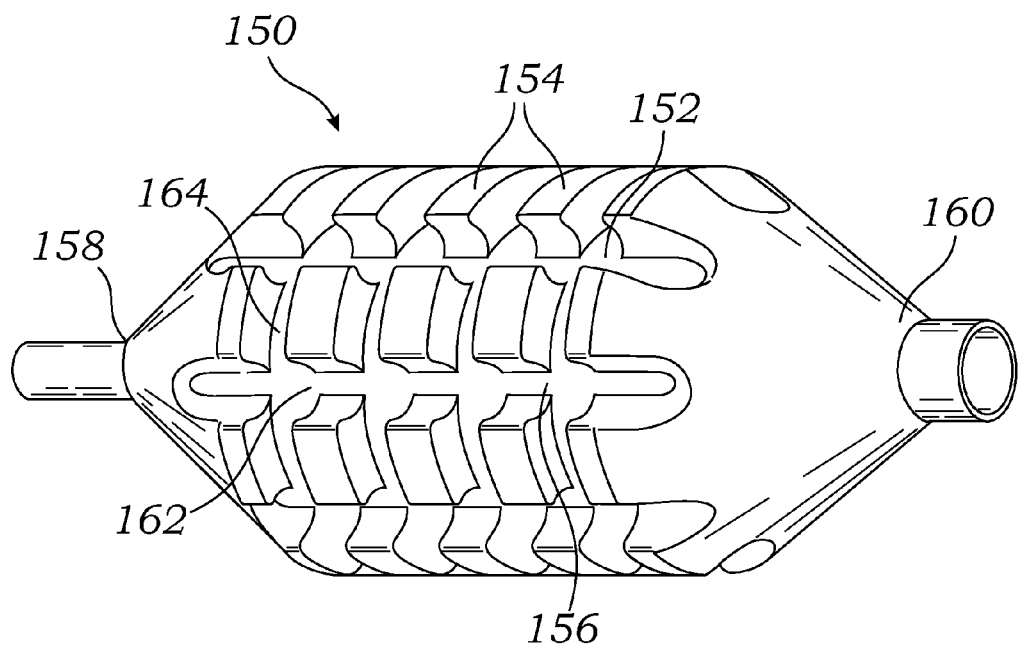
FIG. 15 illustrates an expansion device shown in an expanded state with one or more blood perfusion passageways between a distal and proximal end of the expansion device.

In another embodiment, other expansion devices are provided that prevent and/or minimize distortion of a balloon member when it undergoes high pressure expansion. Referring to FIG. 15, an expansion device 150 with a plurality of projections is disclosed. Expansion device 150 comprises a main body 152 and a plurality of projections 154 that extend radially from main body 152 and circumferentially around the main body. Projections 154 define grooves 156 alone the expansion device 150 to allow blood to pass from a proximal end 158 to a distal end 160 of the expansion device. Projections 154 preferably define both longitudinal grooves 162 and circumferential grooves 164. Longitudinal grooves 162 extend in a substantially longitudinal direction between proximal end 158 and distal end 160, while circumferential grooves 164 extend in a circumferential direction around expansion device 150. Preferably, longitudinal grooves 162 extend substantially the length of the expansion device 150 and circumferential grooves 164 extend substantially around the circumference of the main body 152; however, as long as longitudinal grooves 162 and circumferential grooves 164 collectively form a one or more passageways between the proximal and distal ends 158, 160 of expansion device 150 when expansion device 150 is in an expanded configuration in an orifice or passageway of the body, expansion device 150 can effectively permit blood to pass between the two ends 158, 160.

As noted above, balloon members have a tendency to distort towards a rounded cross-sectional configuration when subjected to high pressures. The circumferential grooves 164 function to minimize the deleterious effects of the inflation pressure. Specifically, because circumferential grooves 164 preferably extend around the circumference of expansion device 150, at those locations the expansion device can achieve a circular cross section when inflated to minimize distortion of expansion device 150 at other locations along the length of the balloon member. In other words, by allowing portions of the expansion device 150 at grooves to achieve a circular cross section, the distortive forces at other locations along the longitudinal axis of expansion device 150 are prevented or at least minimized.

Thus, expansion device 150 can have a plurality of circular cross-sectional areas extending along the length of expansion device 150. In particular, such circular cross-sectional areas can be at the locations of the one or more circumferential grooves. In addition, because expansion device has projections and grooves formed between the projections, the expansion device desirably has a plurality of different cross-sectional shapes/sizes along the length of expansion device 150. For example, the cross section at a circumferential groove can be circular and of a certain size (diameter), while the cross section at other locations can be non-circular and larger in size than the cross section of the circumferential groove.

Figure 16:
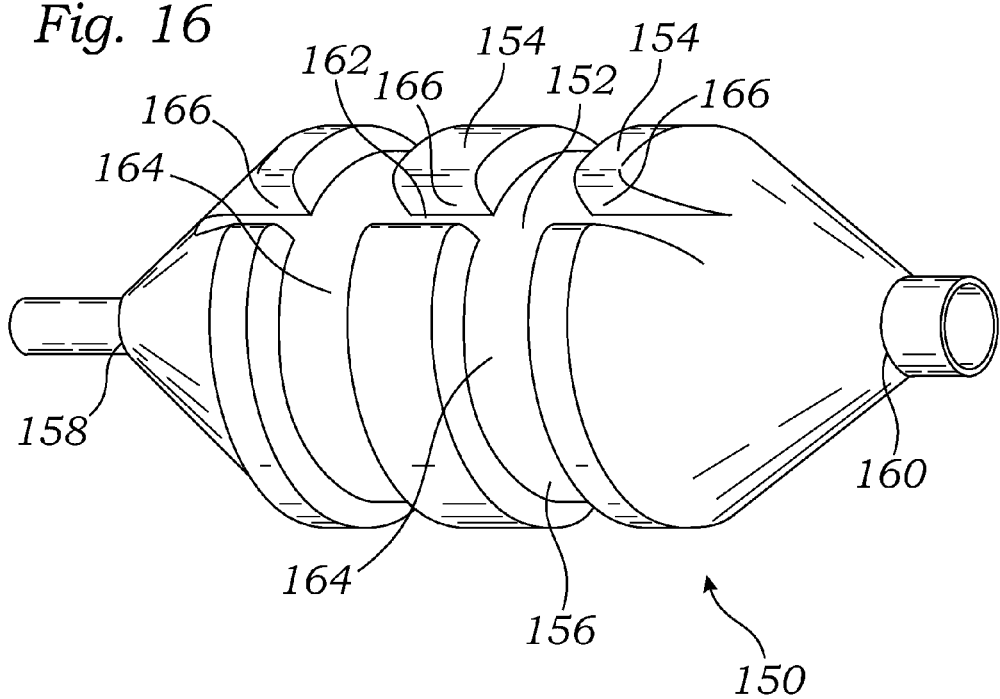
FIG. 16 illustrates an expansion device shown in an expanded state with one or more blood perfusion passageways between a distal and proximal end of the expansion device.

FIG. 16 illustrates another embodiment of an expansion device 150. The expansion device of FIG. 16 comprises fewer projections 154 than that of FIG. 15. In addition, the projections 154 of FIG. 16 are rounded or tapered along the circumferential direction. These rounded portions 166 can reduce the likelihood of "blow-out" of the non-circular sections. As in FIG. 15, longitudinal grooves 162 extend in a substantially longitudinal direction between proximal end 158 and distal end 160, while circumferential grooves 164 extend in a circumferential direction around expansion device 150.

Although each of the expansion devices 150 shown in FIGS. 15 and 16 have projections that are uniformly distributed in a grid-like manner, it should be understood that the projections can be non-uniformly spaced along the main body of expansion device 150.

Figure 17:
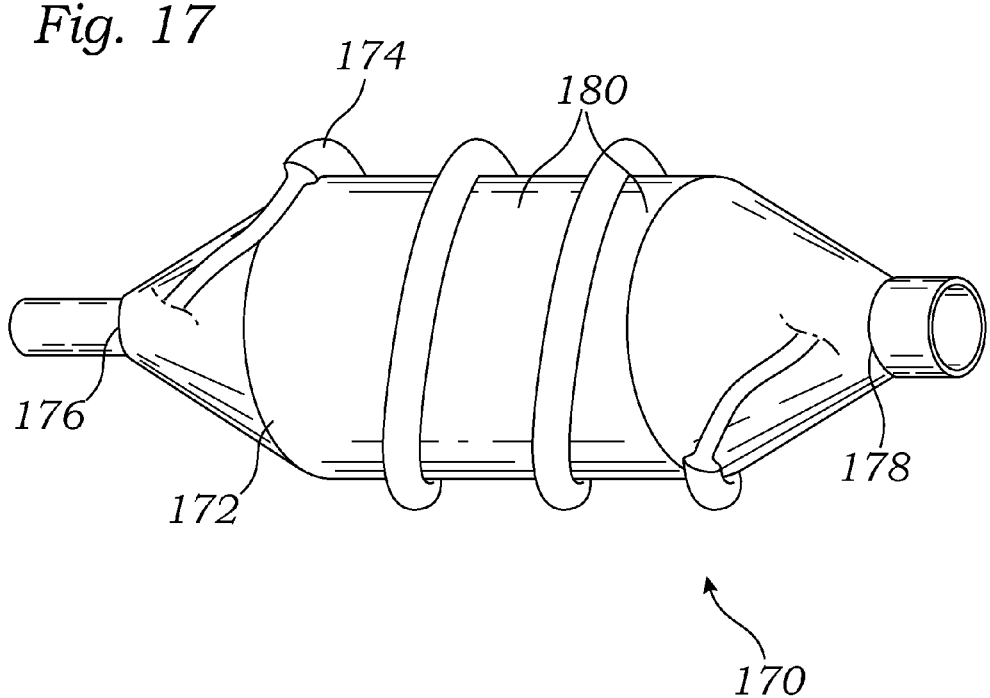
FIG. 17 illustrates an expansion device shown in an expanded state with one or more blood perfusion passageways between a distal and proximal end of the expansion device.

In another embodiment, an expansion device 170 is provided. As shown in FIG. 17, expansion device 170 comprises an inner balloon member 172 and an outer balloon member (or projection) 174 that extends from a proximal end 176 to a distal end 178 of expansion device 170. Outer balloon member 174 extends from proximal end 176 to distal end 178 by wrapping around the main body of inner balloon member 172 one or more times. Preferably, outer balloon member 174 wraps around inner balloon member 172 in the substantially helical manner shown in FIG. 17. Thus, when inner balloon member 172 and outer balloon member 174 are expanded, blood can perfuse between the proximal and distal ends 176, 178 through a passageway 180 formed between adjacent radially projecting portions of the outer balloon member 174. If the outer balloon member 174 extends around a surface of the inner balloon member 172 in a substantially helical configuration, the resulting passageway will also be substantially helical in shape.

Outer balloon member 174 is preferably coupled to inner balloon member 172 so as to maintain the helical shape when outer balloon member 174 is expanded. However, it may be preferable to leave portions of outer balloon member free (unattached to inner balloon member 172) so that expansion device 170 can have a smaller reduced profile when the balloon members are deflated. In other words, as described above with respect to the embodiment shown in FIG. 3, the outer balloon member 174 can self-align by moving into gaps in the compressed profile of the expansion device 170.

Figure 18A:
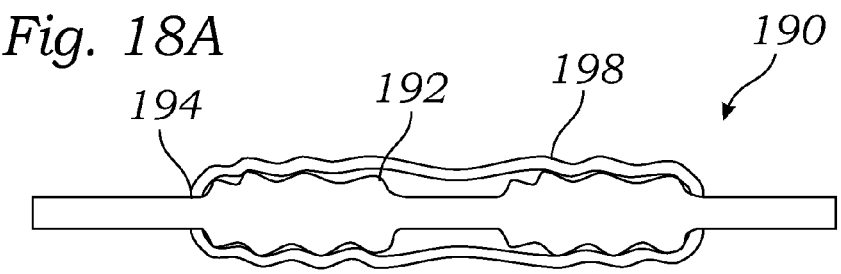
FIG. 18A illustrates a side view of an expansion device with an inner balloon member and a plurality of separate outer balloon members, shown in a collapsed configuration.
Figure 18B:
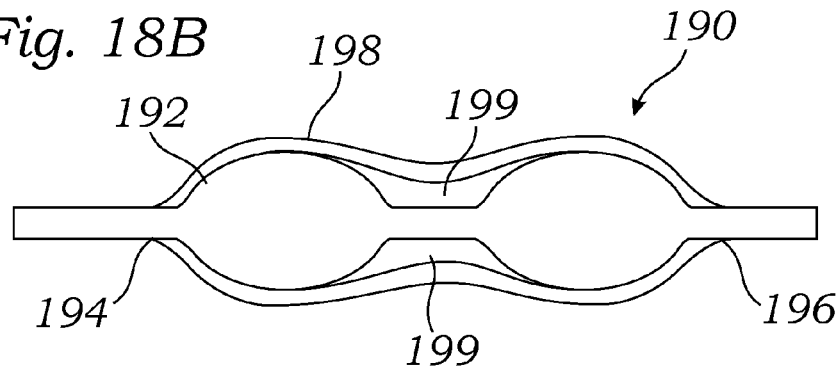
FIG. 18B illustrates a side view of an expansion device of FIG. 18A, shown in an expanded configuration.

As discussed above, balloon members preferably have a round cross section to prevent or reduce the chance of distortion of the balloon member when inflated. Other shapes, however, may be advantageous. For example, FIGS. 18A and 18B illustrate an expansion device 190 similar to that shown in FIGS. 3 and 4, except that the inner balloon member 192 is peanut-or dog bone-shaped. That is, inner balloon member 192 has a wider radius at portions near the proximal end 194 and distal end 196 than at a center portion. A plurality of outer balloon members 198 extends substantially the length of the inner balloon member 192. The outer balloon members can be configured in an identical or substantially similar manner as the outer balloon members of other embodiments. For example, as described above with respect to FIGS. 3 and 4, outer balloon members 198 can be attached to the inner balloon member 192 at the proximal and distal ends 194, 196 such that a central area of each outer balloon member between the proximal and distal ends 194, 196 is left unattached to the inner balloon member.

As discussed above and shown, for example, in FIG. 4, outer balloon members can be configured to provide gaps for perfusion of blood between adjacent balloon members. The use of an inner balloon member that is shaped as shown in FIGS. 18A and 18B can be advantageous when used in combination with a plurality of outer balloon members because it can allow for even more flow between the proximal and distal ends of the expansion device. In particular, because outer balloon member 198 is preferably unattached at a central region, an inner surface of outer balloon members 198 can be spaced apart from the inner balloon member 192 when expanded, defining additional gaps 199 between the outer balloon member 198 and the inner balloon member 192. These additional gaps 199 can further facilitate blood flow between the proximal and distal ends 194, 196.

Moreover, the dog bone-shape of the inner balloon member 192 can help to stabilize the prosthetic valve on the expansion device during the expansion procedure. That is, the prosthetic valve can be mounted on the prosthetic valve between the proximal and distal ends 194, 196 so that at least a portion of the two bulbous or radially enlarged regions (i.e., the wide portions of the dog bone-shaped inner balloon member) extend beyond the proximal and distal ends, respectively, of the prosthetic device.

When deploying a prosthetic valve in an annulus (e.g., the aortic annulus), inner balloon member 192 can be expanded to stabilize the prosthetic valve on the expansion device. By mounting the prosthetic valve between the two bulbous regions of the inner balloon member 192, the prosthetic valve can be firmly held on the inner balloon member 192. If desired, the position of the prosthetic valve within the annulus can be adjusted while the prosthetic valve is firmly mounted on the expansion device. Once the prosthetic valve is in the proper position for deployment, one or more outer balloon members 198 can be expanded as shown in FIG. 18B to fully deploy the prosthetic valve in the annulus. As the outer balloon members 198 expand, outer balloon members 198 press against the inner surface of the prosthetic valve and cause the prosthetic valve to expand to its deployed configuration. Although the outer balloon members 198 are shown in FIG. 18B following the curve of the inner balloon member 192, it should be understood that if sufficient pressure is applied to the outer balloon members 198, they will take on a more rod-like (e.g., straight) shape at the area above gaps 199.

Figure 19A:
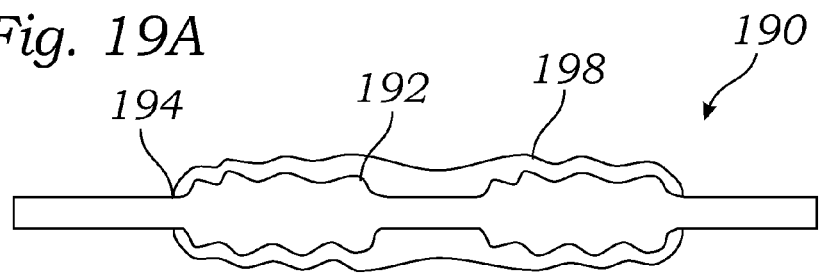
FIG. 19A illustrates a side view of an expansion device with an inner balloon member and an outer balloon member surrounding the inner balloon member, shown in a collapsed configuration.
Figure 19B:
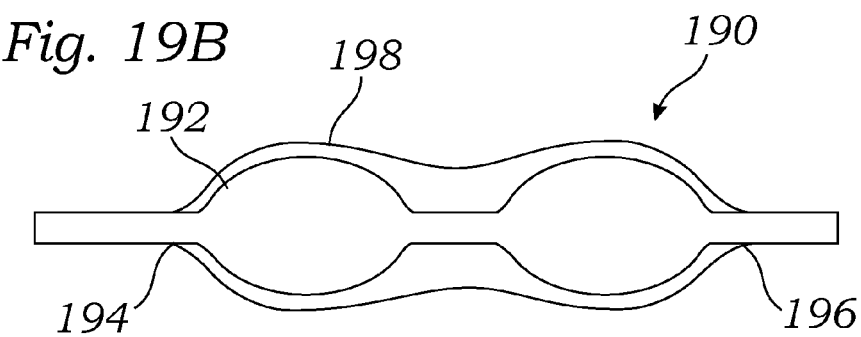
FIG. 19B illustrates a side view of an expansion device of FIG. 19A, shown in a partially expanded configuration.
Figure 19C:
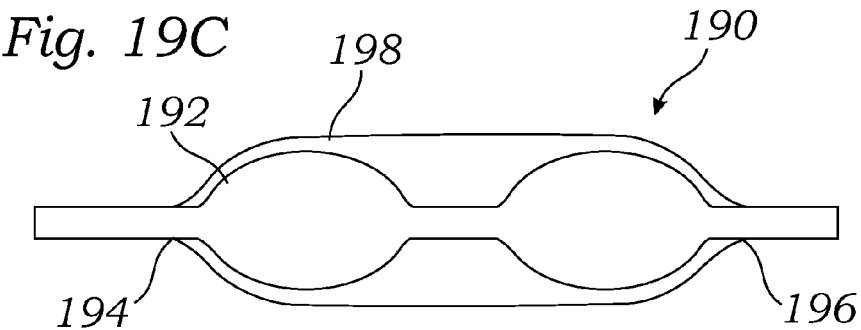
FIG. 19C illustrates a side view of an expansion device of FIG. 19A, shown in an expanded configuration.

FIGS. 19A-19C illustrate another embodiment of an expansion device. The expansion device 190 of FIGS. 19A-19C is similar to that shown in FIGS. 18A and 18B, except that instead of a plurality of outer balloon members, there is a single outer balloon member 198 that surrounds the inner balloon member 192. As in the embodiment, of FIGS. 18A and 18B, the inner balloon member 192 can be expanded to stabilize or secure the prosthetic device on the inner balloon member 192 (FIG. 19B). Then, by expanding the outer balloon member 198, the prosthetic device can be fully deployed within an annulus (FIG. 19C). While the embodiment of FIGS. 19A-19C includes the dog bone-shaped inner balloon member 192, it does not provide for gaps 199 as shown in FIGS. 18A-18B since the outer balloon member 198 fully surrounds inner balloon member 192 in this embodiment.

Figure 20:
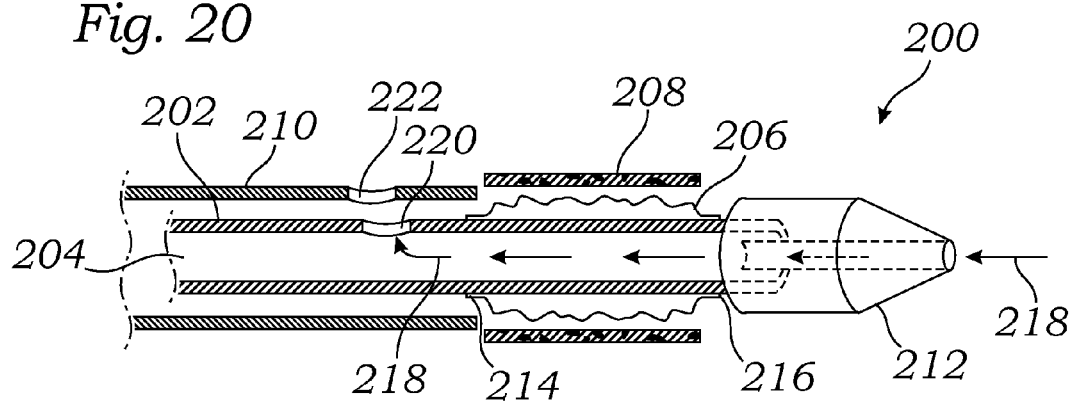
FIG. 20 illustrates a partial cross-sectional view of a delivery system with one or more perfusion lumens.

In other embodiments, other techniques, devices, and methods can be used to increase blood perfusion between proximal and distal ends of an expansion device mounted at the distal end of a delivery device. FIG. 20 illustrates a perfusion device, or catheter assembly, 200 that includes an inner tube, or catheter, 202 with a lumen 204 passing therethrough. A balloon member 206 can extend over a portion of the inner tube 202 and a prosthetic device 208 (e.g., a prosthetic valve) can be crimped onto the balloon member 206. An outer tube, sheath, or catheter, 210 (sheath) can extend along at least a portion of inner tube 202. A nose cone 212 can be provided at a distal end of inner tube 202. Balloon member 206 can comprise a conventional inflatable balloon or one of the expansion devices described herein.

Lumen 204 can be configured to receive a guide wire (not shown). After the prosthetic device is advanced to a deployment position for expansion in the body, the guide wire can be removed from the lumen 204 (or at least removed from the distal end of the lumen) and blood can be allowed to perfuse between a distal end 216 and a proximal end 214 of balloon member 206. Referring to FIG. 20, blood can flow in the direction of arrows 218 through nose cone 212 and lumen 204. To facilitate blood flow out of lumen 204, one or more openings 220 can be provided in inner tube 202. Also, if outer tube 210 is positioned over inner tube 202, outer tube 210 can also comprise a plurality of openings 222. Preferably, the openings 222 in outer tube 210 can be aligned or positioned adjacent to openings 220 in inner tube 202 to facilitate blood flow out of the lumen at the proximal end 214 of balloon member 206.

Figure 21:
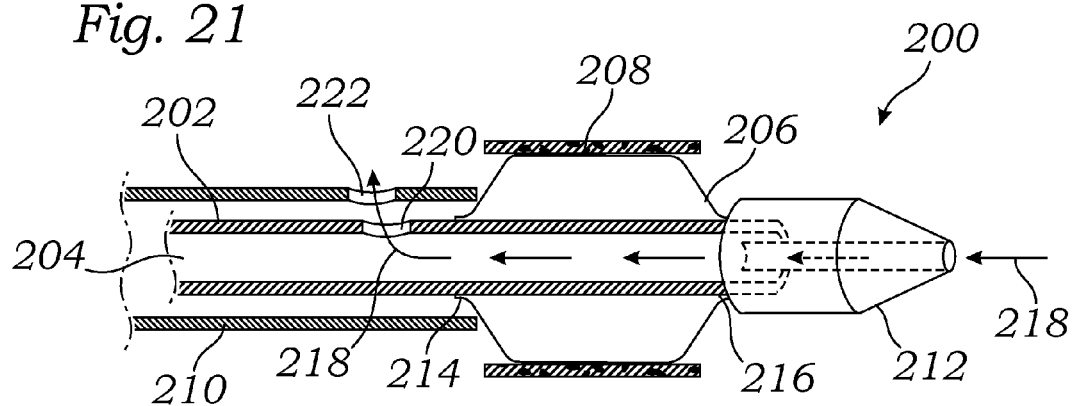
FIG. 21 illustrates a partial cross-sectional view of the delivery system of FIG. 20, shown with an expansion device in an expanded configuration.

FIG. 21 illustrates an expanded configuration of the perfusion device 200 of FIG. 20. As shown in FIG. 21, balloon member 206 can be expanded to deploy prosthetic device 208. During the expansion of balloon member 206, blood flow between the distal and proximal ends of the balloon member 206 can be restricted by balloon member 206. However, by providing an internal passageway (lumen 204) through which blood can flow, the restriction of blood flow through the passageway can be reduced. In addition, if perfusion device 200 is used with the inner and outer balloon member configurations disclosed in other embodiments, blood perfusion can be further increased.

In a modification of perfusion device 200, as shown in FIG. 22, inner tube 202 can comprise a collapsible member or collapsible portion 226. Thus, as shown in FIG. 22, the collapsible member 226 can receive a crimped prosthetic device 208 and achieve a lower profile by collapsing to a smaller diameter when the prosthetic device 208 is crimped thereon. Since blood perfusion through the lumen 204 is primarily required when the balloon member 206 is in an expanded configuration (FIG. 21), the narrowed lumen 204 of collapsible member 226 when the prosthetic device is in a collapsed (crimped) configuration (FIG. 22) does not significantly restrict blood flow.

When the compressive force on the collapsible member 226 is removed by expanding the balloon member 206, the collapsible member 226 desirably returns to a larger diameter configuration (such as is shown in FIG. 21). Conventional tubing material may not recover sufficiently to allow for sufficient blood flow through the lumen. In addition, conventional tubing may kink, break, or otherwise fail when crushed (collapsed) by the force of the crimped prosthetic valve or when later expanded by the inward force applied by the balloon member 206 during inflation. Accordingly, collapsible member 226 is preferably formed of a resilient material, such as Nitinol. In a preferred embodiment, collapsible member 226 comprises a braid formed of Nitinol.

As discussed above, a perfusion lumen can be used in combination with the multi-balloon expansion devices described herein. For example, FIGS. 23 and 24 illustrate expansion devices 250 that include an inner balloon member 252 and a plurality of outer balloon members 254, and which are used in combination with a perfusion lumen 256 of an inner tube 258. Perfusion lumen 256 extends between proximal and distal ends of expansion device 250. Expansion devices 250 of FIGS. 23 and 24 are substantially the same, except that inner balloon member 252 of FIG. 24 has a shape that is substantially peanut-shaped or dogbone-shaped, as described above with regard to FIGS. 18A and 18B. It should be understood that expansion devices 250 can take the form of any expansion devices discussed herein, and lumen 256 can be configured to allow the passage of blood between proximal and distal ends of expansion device as described in any of the embodiments herein.

In other embodiments, the perfusion passageway between proximal and distal ends of the expansion device can comprise one or more lumens. For example, as shown in FIGS. 25A and 25B, a perfusion device, or catheter assembly, 300 comprises a tube 302 that has a single lumen 304 for blood perfusion between a distal end 308 and proximal end 306 of an expansion device 310. An opening 312 in the tube 302 permits blood to flow from the lumen 304. Perfusion of blood through lumen 304 can be achieved in the manner identical to or substantially similar to that described above with respect to FIGS. 20 and 21.

In another embodiment shown in FIGS. 26A and 26B, a perfusion device, or catheter assembly, 320 comprises a tube, or catheter, 322 that has multiple lumens 324 for blood perfusion between a proximal end 326 and distal end 328 of an expansion device 330. One or more openings 332 in the tube 322 permit blood to flow outwardly from the one or more lumens 324. Desirably, tube 322 is formed with at least one opening 332 in fluid communication with each lumen. Again, perfusion of blood through lumens 324 can be achieved in the manner identical to or substantially similar to that described above with respect to FIGS. 20 and 21. However, because there are multiple lumens 324 for blood perfusion, it may be more desirable to include multiple openings 332 that can be aligned with the respective openings in an outer shaft (not shown).

The above embodiments disclose methods for deploying expansion devices in an orifice or passageway of the body. By providing mechanisms for allowing and/or increasing blood perfusion between the expansion devices, a physician can have additional time to deploy (or collapse) the expansion device and the risk of significant adverse effects due to blood occlusion through the orifice or passageway can be reduced.

Additional embodiments are disclosed for securing a prosthetic device to a distal end portion of a delivery device. FIG. 27 illustrates an apparatus and device for releasably securing the prosthetic device using a release wire. A delivery apparatus 400 comprises an inner tube, or catheter, 402 and an outer tube, or catheter, 404 (sheath). A balloon member 406 and nose cone 408 are positioned at a distal end of inner tube 402. A prosthetic device 410 can be secured to the inner tube via one or more tethers (e.g., wires) 412 that extend into respective openings on the prosthetic device 410. Each tether 412 passes through an opening on the prosthetic device 410, and one or more release wires 414 are passed through an opening or loop 416 at the end of a respective tether 412 to secure the prosthetic device 410 to the inner tube. The release wires 414 can be coupled to outer tube 404 and the retraction (proximal movement) of outer tube 404 relative to inner tube 402 can cause release wires 414 to be removed from openings 416 of tethers 412, allowing the loops 416 to be pulled through their respective openings on prosthetic device 410 and thereby releasing prosthetic device 410 from the connection formed by tethers 412 and release wires 414. Alternatively, release wires 414 can extend proximally to a handle (not shown) and be moved or released independently of outer tube 404. In the illustrated embodiment, prosthetic device 410 comprises a stented prosthetic heart valve. The leaflets of the prosthetic valve are omitted for clarity in the figures.

In another embodiment shown in FIG. 28, delivery apparatus 400 comprises hooking members 420 that extend from a distal end of inner tube 402. Hooking members 420 are preferably biased outwards so that a distal end of each hooking member 420 is held against an opening 421 in prosthetic device 410. To release the prosthetic device 410, outer tube 404 can be moved distally relative to inner tube 402 and the hooking members, thereby forcing outwardly-biased hooking members 420 inward as the outer tube passes over the hooking members. As the outward tube 404 moves over the hooking members 420, the hooking members 420 are compressed to the inner diameter of the outer tube, thereby moving the hooking members 420 radially inward and out of engagement with openings 421. Thus, the inward force applied to the hooking members 420 by outer tube 404 releases prosthetic device 420 from hooking members 420.

In other embodiments, the prosthetic device can be secured to the delivery apparatus from both ends to provide further maneuverability of the prosthetic valve after it has been expanded. FIG. 29 schematically (in partial cross section) illustrates a balloon member 450 that has a plurality of securing members 452 for securing a prosthetic device 454 to the balloon member 450. Securing members 452 can comprise holding flaps that extend distally and proximally, respectively, from the balloon member 450. Holding flaps can be formed integral with the balloon member 450 or they can be separate members that are coupled (glued, stitched, etc.) to the balloon member 450. As balloon member 450 deflates, securing members 452 pull away from prosthetic device 454, thereby releasing prosthetic valve 454 from securing members 452.

Figure 30:
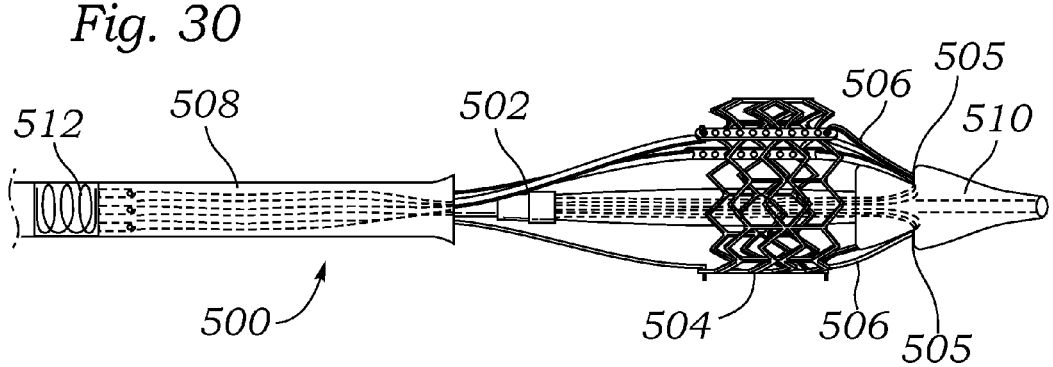
FIG. 30 illustrates a delivery system and a method and apparatus for securing a prosthetic device to a distal end of the delivery system.

FIG. 30 illustrates an embodiment in which a prosthetic device (e.g., a prosthetic heart valve) is coupled to a delivery apparatus 500 at both proximal and distal ends. A hooking member 502 (as discussed above) can be used to secure a proximal end of a prosthetic device 504, while one or more sutures 506 can extend from a proximal end of delivery apparatus 500 to a distal end of prosthetic device 504. For example, sutures 506 can extend through an inner tube 508 from the proximal end of delivery apparatus 500 and outwardly through openings 505 in a nose cone 510 positioned at a distal end of apparatus 500. Sutures 506 can extend from openings 505 and loop over and around (or through) a distal portion of prosthetic device 504. The free end of the sutures can then extend back through inner tube 508 to the proximal end of delivery apparatus 500. From the proximal end of delivery apparatus 500, sutures 506 can be released to release the distal end of prosthetic device 504.

To maintain tension on the distal end of prosthetic device 504, a spring member 512 can be coupled to each end of the sutures 506 that secure prosthetic device 504. For example, if three sutures 506 are used to secure the distal end of the prosthetic device 504 (as shown in FIG. 27), after the sutures 506 loop through the prosthetic device, six ends of the sutures 506 can be secured to a proximal end of delivery apparatus 500 (e.g., at spring member 512).

Figure 31:
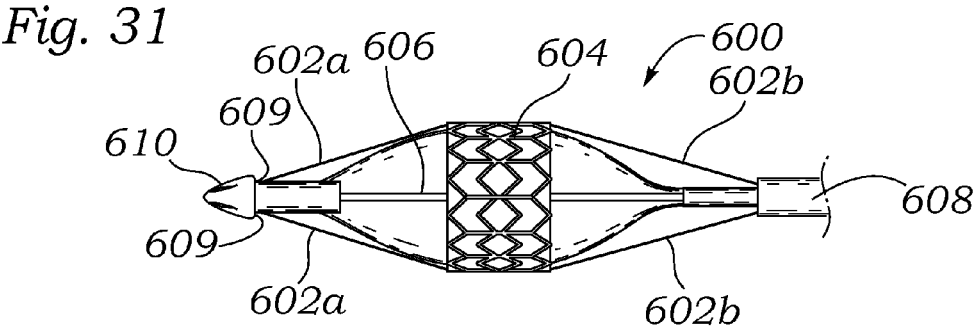
FIG. 31 illustrates a delivery system and a method and apparatus for securing a prosthetic device to a distal end of the delivery system.

FIG. 31 illustrates an embodiment in which a prosthetic device (e.g., a prosthetic heart valve) is coupled to a delivery apparatus 600 at both proximal and distal ends of a prosthetic device 604 using sutures. As shown in FIG. 31, a first set of sutures 602a can extend through an inner tube 606 from the proximal end of the delivery apparatus and out openings 609 in a nose cone 610 positioned at a distal end of delivery apparatus 600. Similarly, a second set of sutures 602b can extend out of inner tube 608 at an area proximal to the prosthetic valve and secure the proximal end of prosthetic device 604. Sutures 602a and 602b can be coupled to prosthetic device 604 any known manner, including for example, using the loops discussed above.

The above structures and methods for hooking or otherwise securing a prosthetic device to a portion of the delivery apparatus can be particularly useful in combination with the multi-stage expansion mechanisms described herein. As a prosthetic device is partially expanded, the forces applied by the balloon member on the prosthetic device can vary and be less predictable than the forces under full expansion, and therefore, the balloon member may not adequately secure or grip the prosthetic valve as it is being expanded to its functional size. Thus, when partially expanding a balloon member or providing a system for expansion of a prosthetic valve in stages, securing mechanism such as those described above can be particularly useful because such securing mechanisms can maintain the prosthetic valve at a fixed position relative to the balloon member to ensure predictable and even expansion of the prosthetic valve. Moreover, such securing mechanism can maintain the prosthetic valve at a fixed position relative o the delivery apparatus after the prosthetic valve is partially expanded to allow the physician to adjust the position of the prosthetic valve (e.g., proximally or distally) within the body lumen relative to the deployment site.

Although many of the embodiments disclosed herein have been described with reference to expanding a prosthetic device, such as a prosthetic heart valve, within an orifice or passageway of the body, it should be understood that the expansion devices and perfusion devices disclosed herein can also be used to perform a valvuloplasty procedure. That is, the expansion of the balloon member(s) can be done without a prosthetic device crimped thereon in a valvuloplasty procedure. The same advantages of blood perfusion described above with respect to an implantation procedure will be present in a valvuloplasty procedure, where no prosthetic device is involved.

Additionally, it should be understood that the expansion device need not comprise all balloon members and, alternatively, can comprise mechanical expansion devices. For example, a mechanical expanding member with an open-frame configuration can comprise the central expanding member around which multiple outer balloon members are positioned.

Figure 32:
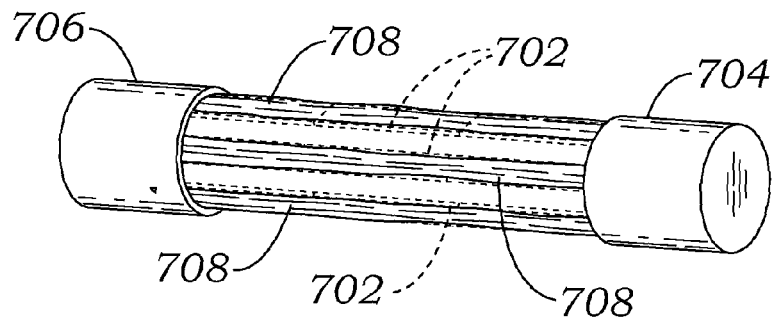
FIG. 32 illustrates an expansion device with a mechanical inner expansion device and a plurality of outer balloon members, shown in a non-expanded (collapsed) configuration.

FIGS. 32-37 disclose an illustrated embodiment of an expansion device (expandable basket) 700 with an open-frame configuration. Expansion device 700 can comprise a plurality of longitudinally-extending, circumferentially-spaced struts 702 terminating and joined together at opposite ends of the expansion device. As shown in FIG. 32, for example, struts 702 can extend between the distal member (cup) 704 and proximal member (cup) 706 of the expansion device 700. Struts 702 can be formed of a variety of materials and in a variety of shapes, as long as the shape and structure is sufficiently strong to cause expansion of a prosthetic device, as described in more detail below. For example, each strut 702 can be formed of a tubular structure of elastic material, such as stiff plastic or metal. In addition, the expansion device 700 can be formed of a variety of number of struts 702, so long as the struts are of sufficient number, strength, and/or shape so as to provide sufficient force to surfaces and/or contact points of the prosthetic device to expand the device as described herein.

Figure 35:
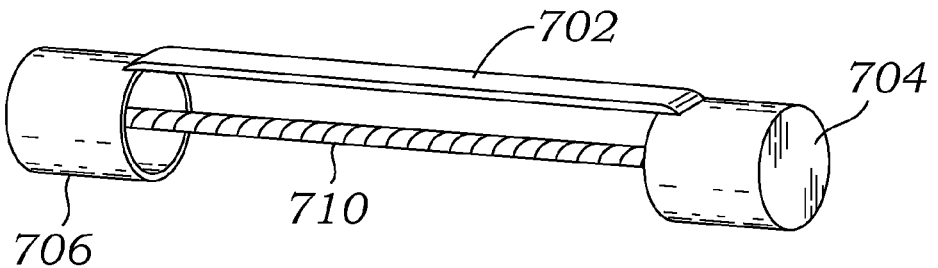
FIG. 35 illustrates an embodiment of the expansion device of FIG. 32 with the outer balloon members and the majority of the struts removed for clarity, shown in a non-expanded (collapsed) configuration.
Figure 36:
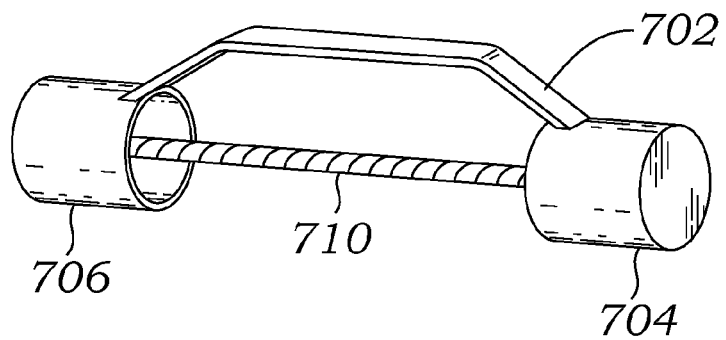
FIG. 36 illustrates an embodiment of the expansion device of FIG. 32 with the outer balloon members and the majority of the struts removed for clarity, shown in an expanded configuration.
Figure 37:
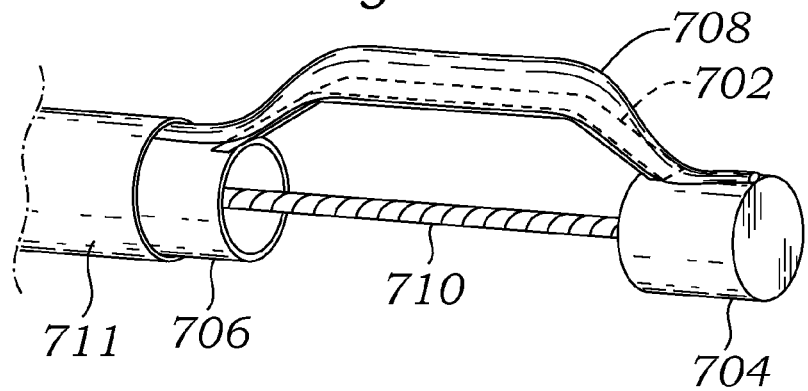
FIG. 37 illustrates an embodiment of the expansion device of FIG. 32 with majority of the outer balloon members and struts removed for clarity, shown in an expanded configuration.

In operation, distal and proximal members 704, 706 can move relative to one another to either expand (by moving closer together) or collapse (by moving further apart) the expansion device 700. The relative movement of the distal and proximal members 704, 706 can be achieved, for example, by translating a central screw mechanism 710 that extends between each member and to which each of the member is threadably connected. Referring to FIGS. 35-37, a method of expanding the expansion device 700 is shown. For convenience, in each of these figures only a single strut 702 is shown. In addition, in FIGS. 35 and 36 the balloon members are removed for clarity. FIG. 35 illustrates the mechanical portion (i.e., strut 702) of expansion device 700 in a collapsed configuration. FIG. 36 illustrates strut 702 in an expanded configuration, where the two cups (distal and proximal members) 704, 706 have moved closer together forcing strut 702 to expand radially. The relative movement of cups 704, 706 can be achieved, for example, by rotation of central screw mechanism 710. Alternatively, cups 704, 706 can be moved closer together (to radially expand struts 702) or further apart (to radially collapse struts 702) using other mechanisms, such as by pulling or pushing on wires or rods attached to one or both of cups 704, 706.

FIG. 37 illustrates strut 702 in a fully expanded configuration with an outer balloon member extending along at least a portion of the surface of strut 702. The other struts and outer balloon members have been removed for clarity. Strut 702 is shown in an expanded configuration with the outer balloon member 708 also expanded. The sequence of expansion can vary. For example, the inner members (struts 702) can be expanded and then the outer balloon members 708 can be expanded, or, alternatively, the outer balloon members 708 can be expanded before the expansion of the inner members (struts 702). Also, as shown in FIG. 37, a catheter 711 can extend distally from the proximal end of the expansion device. Outer balloon members 708 can be expanded by fluid delivered through a lumen within catheter 711.

A plurality of outer balloon members 708 can be coupled to the struts 702. Each outer balloon member 708 is desirably coupled to at least one struts 702 so that it can maintain its position relative to the struts 702. The plurality of struts 702 can each have an outer surface that defines a supporting surface for supporting at least one outer balloon member 708. The width of the supporting surface of each strut can vary. For example, if only one strut 702 supports each outer balloon member 708, the strut and the supporting surface can have a greater width. However, if multiple struts 702 support a single outer balloon member 708, the width of the strut and support surface can be smaller Each strut 702 in the annular array can be laterally deformable to radially expand or radially contract the annular array of struts 702, and the supporting surfaces defined by them.

Figure 33:
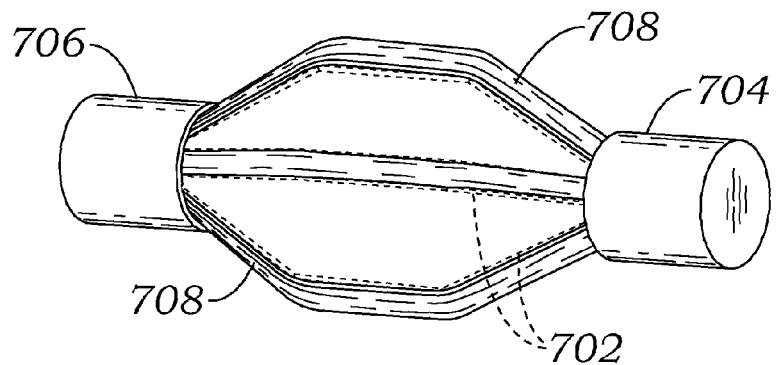
FIG. 33 illustrates an expansion device with a mechanical inner expandable member and a plurality of outer balloon member, shown in a partially expanded configuration.
Figure 34:
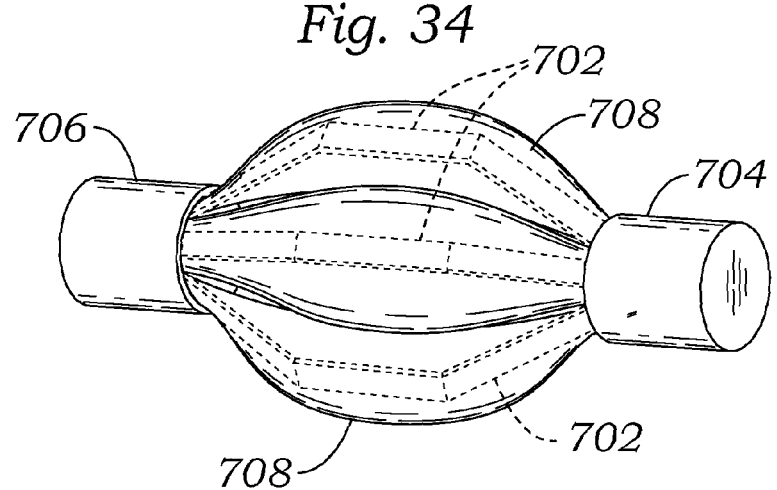
FIG. 34 illustrates an expansion device with a mechanical inner expandable member and a plurality of outer balloon member, shown in an expanded configuration.

In operation, struts 702 can function similar to the inner balloon members disclosed herein. That is, struts 702 have a collapsed configuration (FIG. 32) and an expanded configuration (FIG. 33). FIG. 33 illustrates the struts 702 in an expanded configuration with outer balloon members remaining in a collapsed configuration. When expansion device 700 is expanded, the supporting surfaces of the struts 702 will push the outer balloon members 708 radially outwards against a prosthetic device (not shown) mounted thereon.

As discussed in other embodiments, the expansion device can be expanded in stages such as a first stage where only the struts 702 are expanded (to partially expand the prosthetic device) and a second stage where the struts 702 and outer balloon members 708 are expanded (to fully expand the prosthetic device). In addition, outer balloon members 708 are preferably expandable independent of the mechanical components (e.g., struts) of expansion device 700. Thus, for example, outer balloon members 708 can be expanded when the struts 702 of expansion device 700 are in a collapsed state (FIG. 32) or a completely expanded state (FIG. 33). Because outer balloon members are independently expandable, outer balloon members 708 can be expanded either before or after the expansion of struts 702. That is, as described in other embodiments herein, the sequence of expansion of the inner member (struts 702) and outer members (outer balloon member 708) can vary.

Expansion device 700 can be particularly advantageous in delivering prosthetic heart valves because the mechanical struts 702 provide significant expansion while at the same time allowing blood to pass around adjacent outer balloons and through the largely hollow internal portion of expansion device 700. Referring to FIGS. 36 and 37, for example, it can be seen that the internal area (i.e., the area beneath the outer balloon members 708) of expansion device 700 is mostly empty space which allows for significant blood perfusion through that portion of expansion device 700. In contrast, when the inner member is a balloon member, the inner balloon member occupies a large portion of the inner area of the expansion device and prevents blood perfusion through that portion of the expansion device. Expansion device 700 is also particularly advantageous because it combines the perfusion capabilities of a mechanical expansion member (e.g., struts 702) with the high pressure expansion strength associated with balloon expansions members.

FIGS. 38A-38C illustrate a method of deploying a prosthetic heart valve within a native aortic annulus. Referring to FIG. 38A, a delivery device 720 is shown delivering a prosthetic heart valve 722 in a collapsed configuration. Delivery device 720 can deliver prosthetic valve 722 to the treatment location using known procedures. For example, the prosthetic device can comprise a SAPIEN Transcatheter Heart Valve (THV) available from Edwards Lifesciences LLC and the prosthetic valve can be delivered either through a transfemoral or transapical approach.

Prosthetic valve 722 can be mounted on an expansion device 724, which can be, for example, an expansion device of the type described herein with reference to FIG. 3. Prosthetic valve 722 is maneuvered within a native aortic valve annulus 726 for deployment using delivery device 720. Referring to FIG. 38B, expansion device 724 is expanded by inflating the inner balloon member and the outer balloon members of the expansion device 724. As illustrated by arrows B, blood can flow between the proximal end 728 and distal end 730 of expansion device 724 through the perfusion pathways provided by the gaps 734 in the expansion device 724 as described and shown herein (e.g., FIG. 4). After prosthetic device 722 is deployed within the native aortic annulus 726, expansion device 724 can be collapsed (deflated) and removed from the aortic annulus (FIG. 38C).

Figure 40:
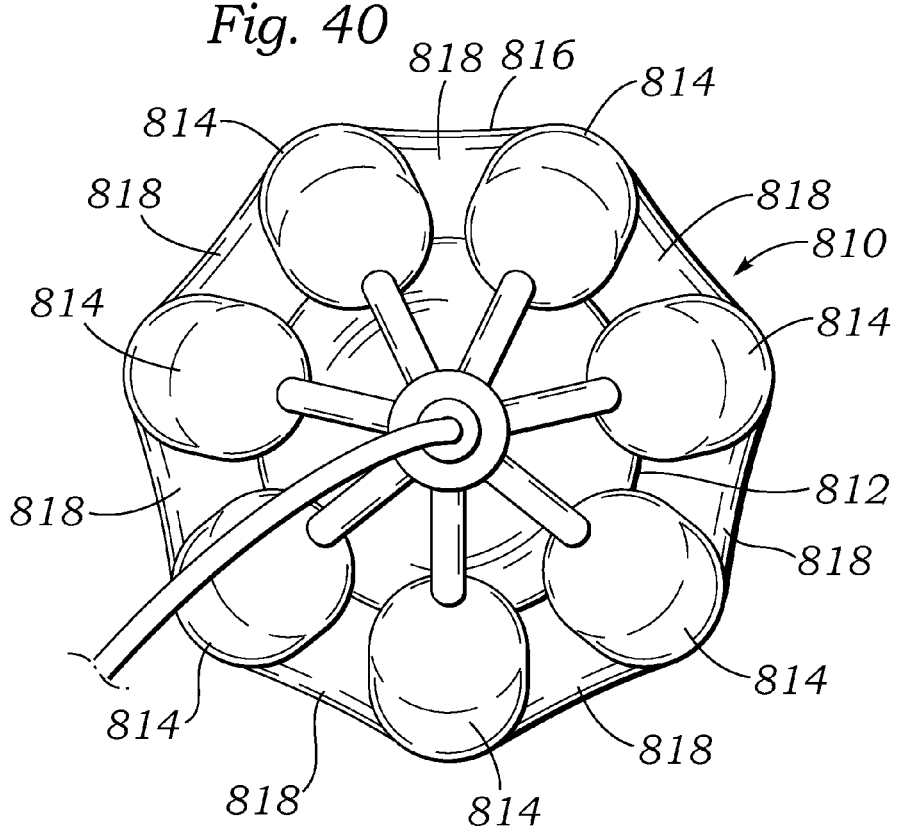
FIG. 40 illustrates a prosthetic heart valve mounted on an expansion device.

As discussed above, the number and size of outer balloon members (e.g., balloon members 52 in FIG. 3) can vary. When the expansion device is used to expand a prosthetic heart valve (e.g., as shown in FIG. 40), the expansion device desirably expands to outer profile that engages with and expands the prosthetic heart valve to a shape that conforms to the anatomy of the native annulus. Thus, for example, when expanding a prosthetic heart valve within the annulus of a native aortic valve, it can be desirable to expand the prosthetic heart valve into a generally round cross-sectional shape.

Generally, an expansion device can achieve a rounder outer profile by increasing the number of outer balloon members 52. However, a larger number of outer balloon members 52 will generally result smaller gaps being formed between adjacent outer balloon members, which can reduce the total flow area across the expansion device. Accordingly, in some embodiments, an expansion device has outer balloon members of a particular orientation and size so that the expansion device is capable of expanding a prosthetic heart valve to a generally round cross-sectional shape while providing a large enough flow area across the expansion device to permit a sufficient amount of blood perfusion between the proximal and distal ends of the expansion device.

In some embodiments, when the expansion device is in its expanded configuration, it can be desirable to provide an amount of flow area across the expansion device that is substantially equal to or greater than an effective orifice area (EOA) of the native valve that is being replaced by the prosthetic heart valve. In this manner, the same amount of blood perfusion across the native annulus can be achieved with the expansion device in an expanded state within the native annulus as was possible before the expansion device was positioned within the native annulus.

Figure 39:
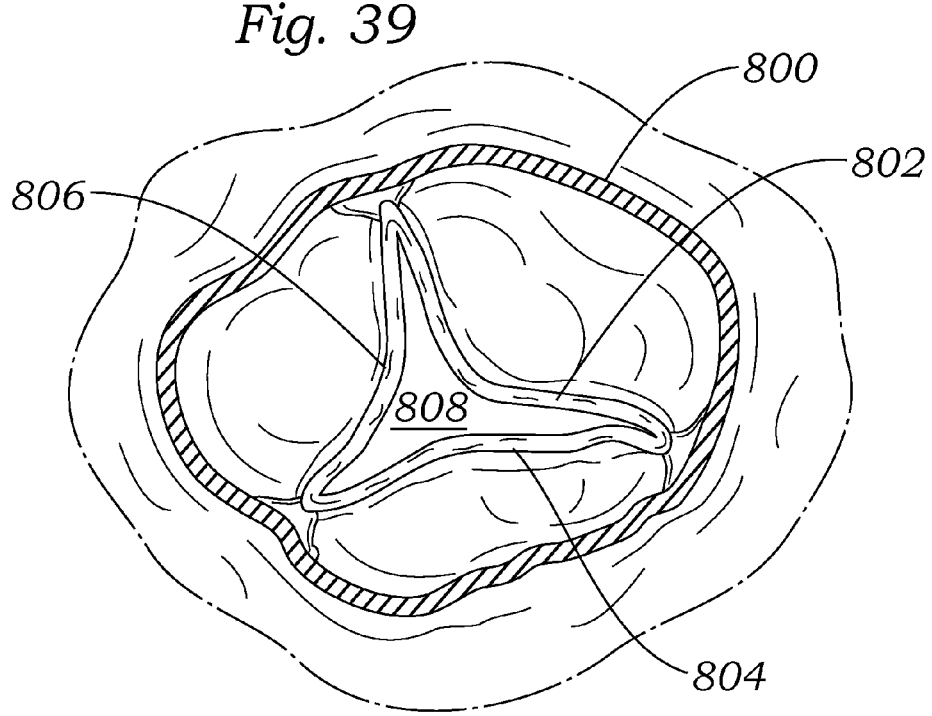
FIG. 39 is a schematic view a calcified native aortic valve annulus.

As noted above, calcification of a native aortic valve can significantly reduce the size of the orifice. FIG. 39 is a schematic view of a calcified native aortic valve 800 during ventricular systole (e.g., in an open state). As seen in FIG. 39, because of calcification of native aortic valve 800, the three native leaflets 802, 804, 806 cannot fully open, which results in a reduced EOA 808 for native aortic valve 800. The EOA of a calcified aortic valve is generally estimated to be between about 0.5 $cm^2$ and 0.7 $cm^2$. For example, the EOA for a native aortic valve annulus having a diameter of about 23 mm the EOA is estimated to be about 0.56 $cm^2$ and the EOA for a native aortic valve annulus having a diameter of about 26 mm is estimated to be about 0.65 $cm^2$.

FIG. 40 illustrates an expansion device 810 that is similar to expansion device 28 shown in FIG. 4. Expansion device 810 has an inner balloon member 812 and seven outer balloon members 814. A prosthetic heart valve 816 can be mounted on the outer surfaces of outer balloon members 814. As seen in FIG. 40, the seven outer balloon members 814 are of sufficient number and size that, upon expansion of expansion device 810, outer balloon members 814 urge against prosthetic heart valve 816 and expand it to a generally round cross-sectional shape. Gaps 818 are formed between adjacent outer balloon members 814 to provide a total flow area that is equal to or exceeds the flow area of the BOA of the calcified native aortic valve 800 shown in FIG. 39.

Accordingly, for a 23 mm prosthetic heart valve, a total flow area provided between the outer balloon members 814 is equal to or greater than about 0.56 $cm^2$. For a 26 mm prosthetic heart valve, a total flow area provided between the outer balloon members 814 is equal to or greater than about 0.65 $cm^2$. For native aortic valves of any size, the total area of gaps at any location along the length of expansion device 810 is preferably greater than 0.7 $cm^2$ to ensure that the flow area equals or exceeds the flow area of the EOA of the calcified native aortic valve. Thus, by providing a total area for blood perfusion that is greater than 0.7 $cm^2$, a patient's blood flow condition will not be made worse during delivery of a prosthetic heart valve mounted on expansion device 810.

Table 1 below illustrates estimated total flow areas achieved by expansion devices that have seven outer balloon members. It should be understood that an outer diameter of an expansion device generally corresponds to the size of the prosthetic heart valve being expanded by the expansion device.

TABLE 1

| Prosthetic heart valve size (diameter) | Inner balloon member (diameter) | Outer balloon members (diameter) | Total flow area between gaps adjacent outer balloon members | EOA of calcified native aortic valve |
|---|---|---|---|---|
| 23 mm | 11 mm | 6 mm | 1.2 cm$^2$ | 0.56 cm$^2$ |
| 26 mm | 13 mm | 6 mm | 1.8 cm$^2$ | 0.65 cm$^2$ |

As shown in Table 1 above, the total flow area of 23 mm and 26 mm prosthetic heart valves can be about twice that of the EOA of a calcified aortic annulus (e.g., 1.2>2(0.56) and 1.8>2(0.65)). Thus, in some embodiments, a total flow area of an expansion device can be greater than about twice the flow area of an EOA of a calcified valve.

For a prosthetic heart valve that has a desired expanded size of about 23 mm, the inner balloon member preferably has a diameter that is between about 10 and 12 mm (more preferably about 11 mm) and the outer balloon members preferably have a diameter that is between about 5 and 7 mm (more preferably about 6 mm). For a prosthetic heart valve that has a desired expanded size of about 26 mm, the inner balloon member preferably has a diameter that is between about 12 and 14 mm (more preferably about 13 mm) and the outer balloon members preferably have a diameter that is between about 5 and 7 mm (more preferably about 6 mm)

Other size expansion devices can be utilized while still providing the desired flow areas described above. For example, prosthetic heart valves can be provided with diameters smaller than the 23 mm and 26 mm prosthetic heart valves shown in Table 1, such as 20 mm, and with diameters larger than the 23 mm and 26 mm prosthetic heart valves shown in Table 1, such as 29 mm. For each size expansion device, the inner balloon member and outer balloon members are preferably sized to provide a desired amount perfusion across the expansion device. For example, in some embodiments, each expansion device can be sized to provide an amount of flow area that is greater than about 0.7 cm$^2$ and/or an amount greater than or equal to the EOA of the calcified valve.

In addition, in some embodiments, expansion device 810, like the other expansion devices described herein, can be used for valvuloplasty procedures. In such procedures, the expansion devices can be configured to provide an outer diameter that can be used to achieve the desired amount of perfusion across the expansion device during a valvuloplasty procedure. The outer diameter of the expansion devices can be generally the same as the size of the prosthetic heart valves described above. Alternatively, in some embodiments, it may be desirable to provide expansion devices that expand to an outer diameter that is smaller than those used for prosthetic heart valve expansion. For example, expansion devices that expand to an outer diameter of about 16 mm or 17 mm can be provided. Of course, if desired, such smaller size expansion devices could also be used to expand similarly sized prosthetic heart valves.

Figure 41:
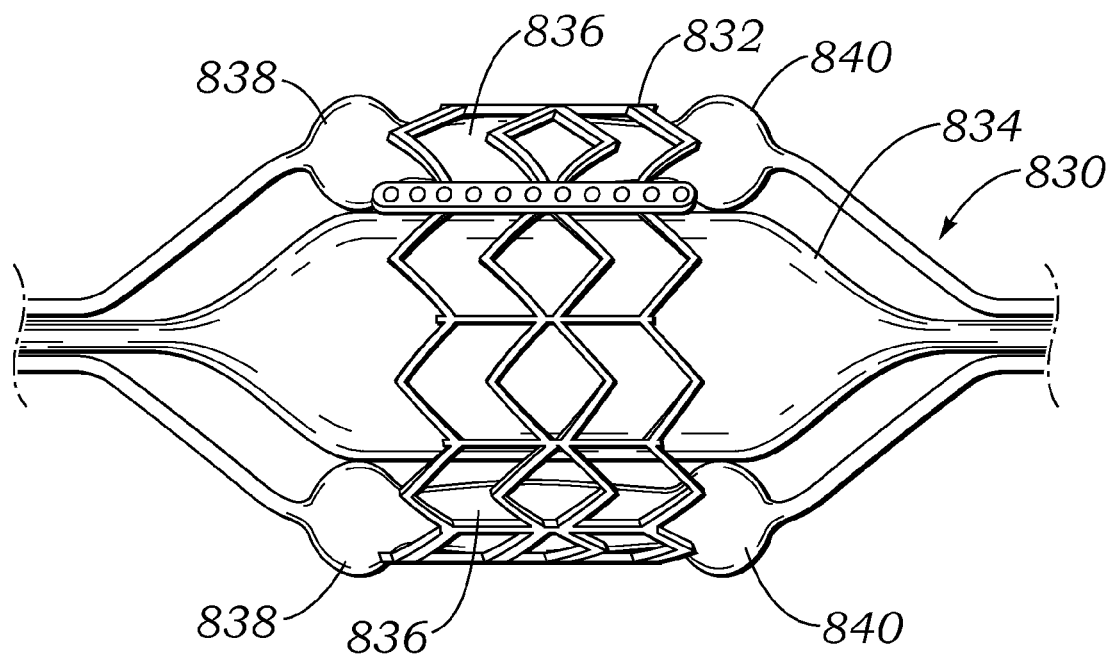
FIG. 41 illustrates another embodiment of a prosthetic heart valve mounted on an expansion device.

FIG. 41 illustrates another embodiment of an expansion device 830 configured to expand a prosthetic heart valve 832 within a native annulus. As in other embodiments described herein, an inner balloon member 834 is surrounded by a plurality of outer balloon members 836. One or more of outer balloon members 836 can comprise enlarged portions at one or both ends of the mounted prosthetic heart valve 832. For clarity, expansion device 830 is illustrated in FIG. 41 with only two outer balloon members 836; however, it should be understood that the number of outer balloon members can be the same as disclosed in other embodiments, such as the seven balloon embodiment shown in FIG. 4 or the eight balloon embodiment shown in FIGS. 5A and 5B.

One or more outer balloon members 836 can have a proximal enlarged portion 838 and a distal enlarged portion 840. For example, each of the outer balloon members 836 can have enlarged portions 838, 840. Alternatively, fewer than all of outer balloon members 836 can have enlarged portions 838, 840, since as few as one outer balloon members 836 with enlarged portions 838, 840 can help to retain prosthetic heart valve 832 on expansion device 830.

The distance between proximal and distal enlarged portions 838, 840 can be large enough to receive the length of a crimped and/or expanded prosthetic heart valve 832 therebetween. In this manner, outer balloon members can have a peanut- or dumbbell-like shape that can help maintain prosthetic heart valve 832 on the generally flat, central portion of outer balloon members 836 between the two enlarged portions 838, 840. When expansion device 830 is collapsed, the additional material associated with enlarged portions 838, 840 can help retain prosthetic heart valve 832 in a crimped configuration (not shown) on expansion device 830. When expansion device is fully expanded (FIG. 41), enlarged portions 838, 840 are located adjacent the two ends of prosthetic heart valve 832, thereby restricting movement of prosthetic heart valve 832 relative to outer balloon members 836.

Figure 42:
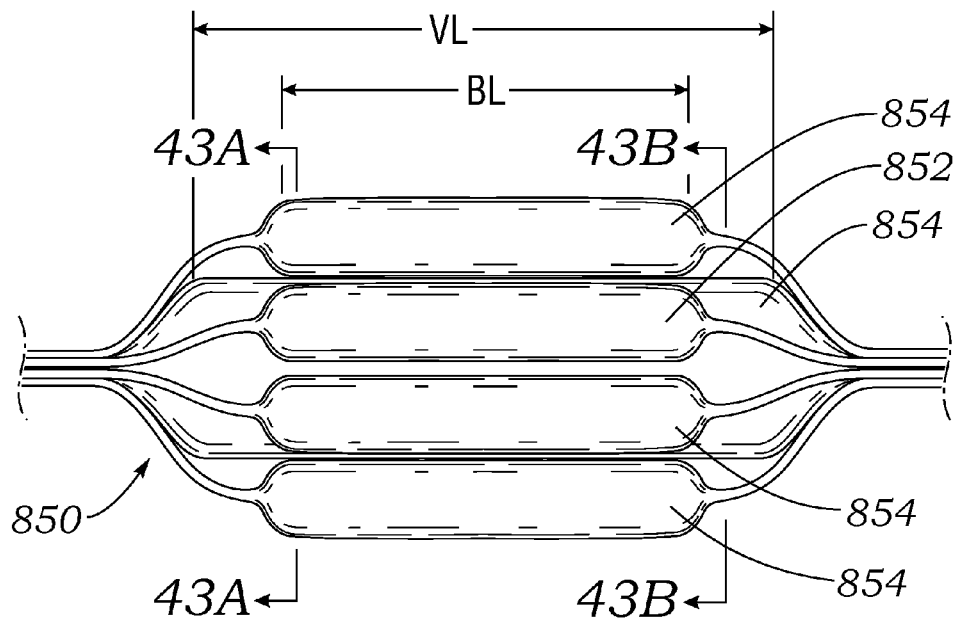
FIG. 42 illustrates an embodiment of an expansion device with a plurality of outer balloon members that have a shorter working length.
Figure 43A:
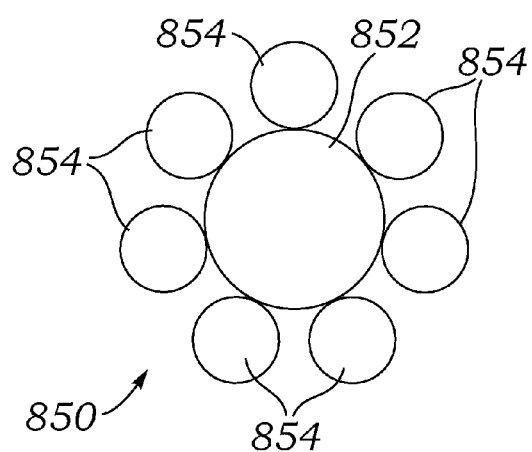
FIG. 43A is a cross-sectional view taken along line 43A-43A of FIG. 42.
Figure 43B:
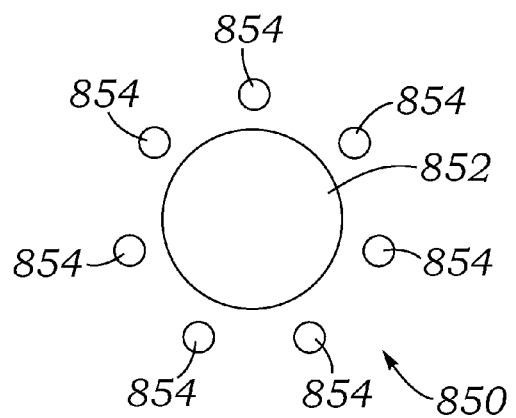
FIG. 43B is a cross-sectional view taken along line 43B-43B of FIG. 42.
Figure 44:
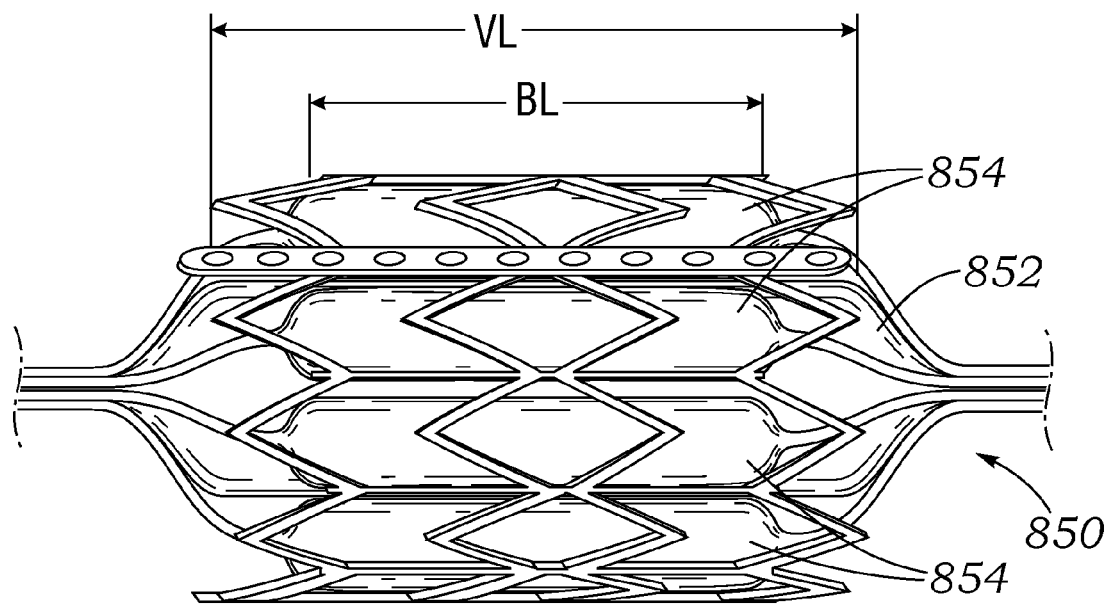
FIG. 44 illustrates a prosthetic heart valve mounted on the expansion device shown in FIG. 42.

FIGS. 42-44 illustrate another embodiment of an expansion device 850. Expansion device 850 also comprises an inner balloon member 852 and a plurality of outer balloon members 854 as described in other embodiments herein. However, the portion of outer balloon members 854 that comes into contact with the valve has a length BL. Balloon length BL can also be referred to as the "working length" or "working portion" of the balloon since it is the portion of the balloon that contacts and urges against a prosthetic heart valve causing the prosthetic heart valve to expand.

In some embodiments, the working length BL of at least some of outer balloon members 854 is shorter than the length VL of the prosthetic heart valve. By reducing the working length BL of the outer balloon member, greater blood perfusion can be achieved across expansion device 850. That is, the distance that blood must flow through the gaps in the outer balloon members is shortened, increasing the rate of blood flow across expansion device 850.

FIGS. 43A is a cross-sectional view taken along a working portion of outer balloon members 854 (i.e., a portion that urges against and expands the prosthetic heart valve). FIG. 43B is a cross-sectional view taken along a non-working portion of outer balloon members 854 (i.e., a portion that includes reduced-profile tail portions that do not urge against and expand the prosthetic heart valve). Higher rates of blood flow can be achieved across expansion device 850 in the area of the reduced-profile tail portions (i.e., the non-working portions of the outer balloon members) because there are larger gaps or openings between adjacent outer balloon members 854 in that area as shown in FIG. 43B.

FIG. 44 illustrates a prosthetic heart valve 856 expanded on the shorter, outer balloon members 854. As described above, blood can pass more easily through the shorter passageways provided by the gaps between adjacent outer balloon members 854, thereby permitting a greater amount of blood to perfuse across expansion device 850.

Figure 45:
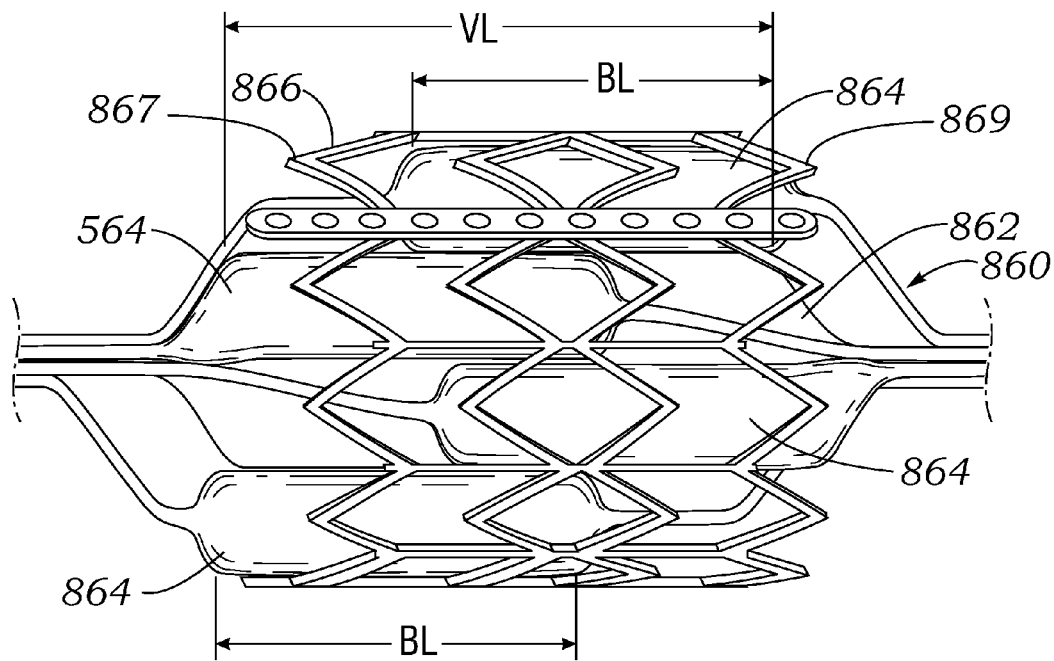
FIG. 45 illustrates another embodiment of a prosthetic heart valve mounted on an expansion device.

FIG. 45 illustrates another embodiment of an expansion device 860. Expansion device 860 also comprises an inner balloon member 862 and a plurality of outer balloon members 864 as described in other embodiments herein. However, at least some of the outer balloon members 864 have a working length BL that is shorter than the length of the valve VL. As described in the previous embodiment, by reducing the working length BL of an outer balloon member, greater blood perfusion can be achieved across the expansion device.

In addition to having one or more outer balloon members 864 that have a working length BL that is less than the length VL of a prosthetic heart valve 866 mounted on expansion device 860, adjacent outer balloon members 864 can be staggered longitudinally so that they are not aligned with one another along the length of inner balloon member 862. Thus, for example, some outer balloon members 864 can be shifted towards a proximal end 867 of prosthetic heart valve 866 so that they are not positioned directly under prosthetic heart valve 866 at its distal end 869. Other outer balloon members 864 can be shifted toward the distal end 869 of prosthetic heart valve 866 so that they are not positioned directly under prosthetic heart valve 866 at its proximal end 867. In some embodiments, outer balloon members 864 can be alternately staggered, as shown in FIG. 45, so that adjacent outer balloon members 864 alternate from being shifted toward one side of proximal heart valve 866 to the other.

By providing the staggered and/or alternating arrangements described above, blood perfusion across expansion device 860 can be increased. In addition, such a staggered arrangement can reduce the collapsed profile of expansion device 860 because less balloon material is required to produce a balloon with a shorter working length.

Figure 46:
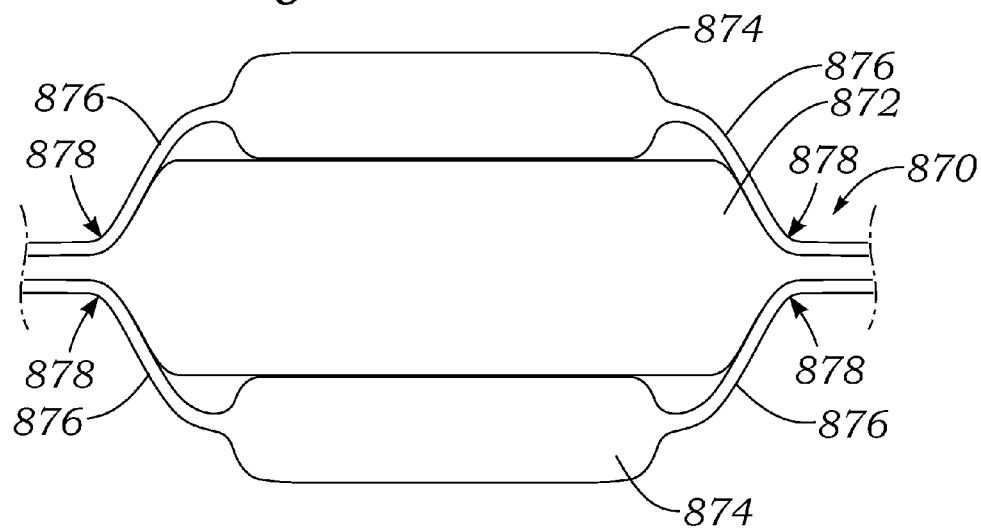
FIG. 46 illustrates another embodiment of an expansion device with portions of the outer balloon members attached to an outer surface of the inner balloon member.

FIG. 46 illustrates another embodiment of an expansion device 870. Expansion device 870 also comprises an inner balloon member 872 and a plurality of outer balloon members 874 as described in other embodiments herein. FIG. 46 is a cross-sectional view of expansion device 870 taken along a longitudinal centerline of the expansion device and showing only two of the plurality of outer balloon members 874.

Each outer balloon member 874 has a tail portion 876 that extends from a proximal or distal end of each outer balloon member 874. The tail portions 876 are preferably attached to a portion of inner balloon member 872 to achieve better control of outer balloon members 874 as they collapse and expand. Thus, for example, tail portions 876 can be fused or otherwise coupled to inner balloon member 872 at connection points 878. By attaching tail portions 876 as close as possible to the body of inner balloon member 872, movement of outer balloon members 874 relative to inner balloon member 872 can be restricted, providing a consistent expansion device.

In addition to fusing and/or coupling tail portions 876 of outer balloon members 874 to inner balloon member 872 as shown in FIG. 46, in some embodiments, adjacent outer balloon members 874 can be fused and/or fixedly coupled to one another to further control the movement of outer balloon members 874 relative to each other and inner balloon member 872.

Figure 47A:
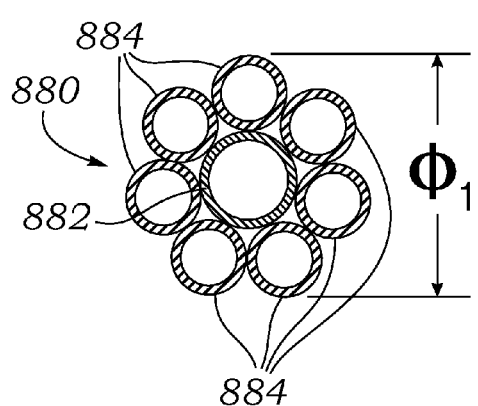
FIG. 47A illustrates another embodiment of an expansion device with tail portions coupled and/or fused together.
Figure 47B:
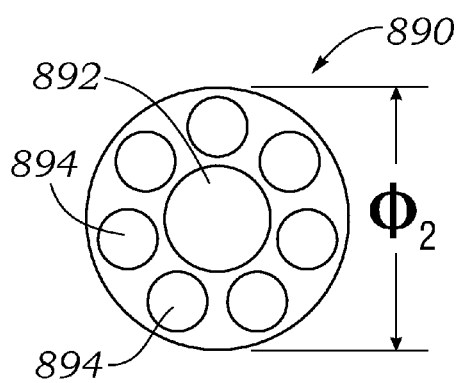
FIG. 47B illustrates another embodiment of an expansion device with tail portions fused together.

The coupling of adjacent outer balloon members to one another and/or to the inner balloon member can be achieved by coupling the balloon material together. FIGS. 47A and 47B illustrate embodiments of coupled tail portions. FIG. 47A illustrates a cross-sectional view of a tail portion of an expansion device 880 that comprises an inner balloon member 882 and a plurality of outer balloon members 884. Each outer balloon member is secured to an adjacent outer balloon member and to the inner balloon member.

In the embodiment shown in FIG. 47B, instead of simply coupling the tail portions together, the tail portions shown in FIG. 47A can be fused together to form an integrated expansion device 890 with a plurality of lumens (i.e., one inner balloon lumen 892 and seven outer balloon lumen 894). Fusing the tail portions together in this manner can provide for better control of expansion device by reducing movement between adjacent balloon members. In addition, by fusing each of the tail portions together, a diameter of that area of the expansion device can be reduced from a first larger diameter $\Phi 1$ (FIG. 47A) to a second smaller diameter $\Phi 2$ (FIG. 47B) due to the use of shared wall sections between adjacent, fused balloon members. Accordingly, not only can the relative movement of balloon members be reduced and/or controlled by fusing adjacent balloon members together as described above, but the profile of the expansion device can be further reduced.

Figure 48A:
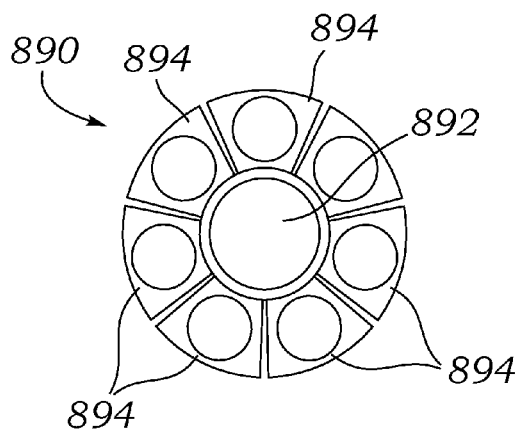
FIGS. 48A and 48B illustrate another embodiment an expansion device with tail portions fused together.
Figure 48B:
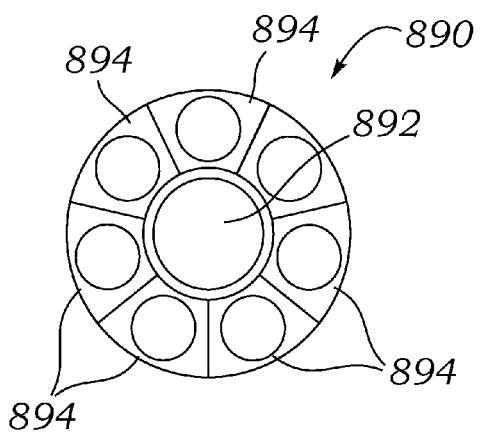

FIG. 48A and 48B illustrate a method for fusing tail portions of expansion member 890 by pre-shaping the tails of outer balloon members 894 into a segment or shape that can facilitate fusing of adjacent tail portions. For example, to facilitate the fusing process, it can be desirable to pre-shape the tails into wedge-shaped portions so that each outer balloon members can be fused to the outer balloon members that are adjacent to it as shown in FIG. 48B. The tail portions can then be fused together by placing the pre-shaped tail portions into a fixed, hot metal die.

Figure 49:
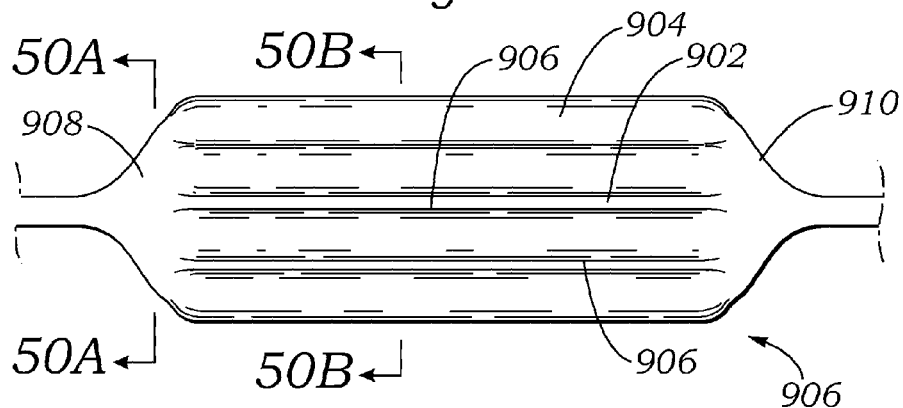
FIG. 49 illustrates an embodiment of an expansion device formed from a single balloon member.
Figure 50A:
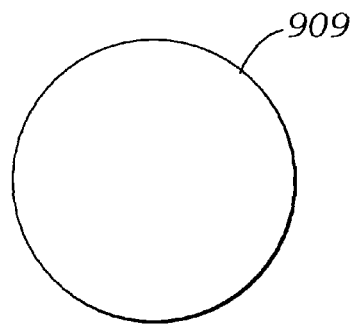
FIG. 50A is a cross-sectional view taken along line 50A-50A of FIG. 49.
Figure 50B:
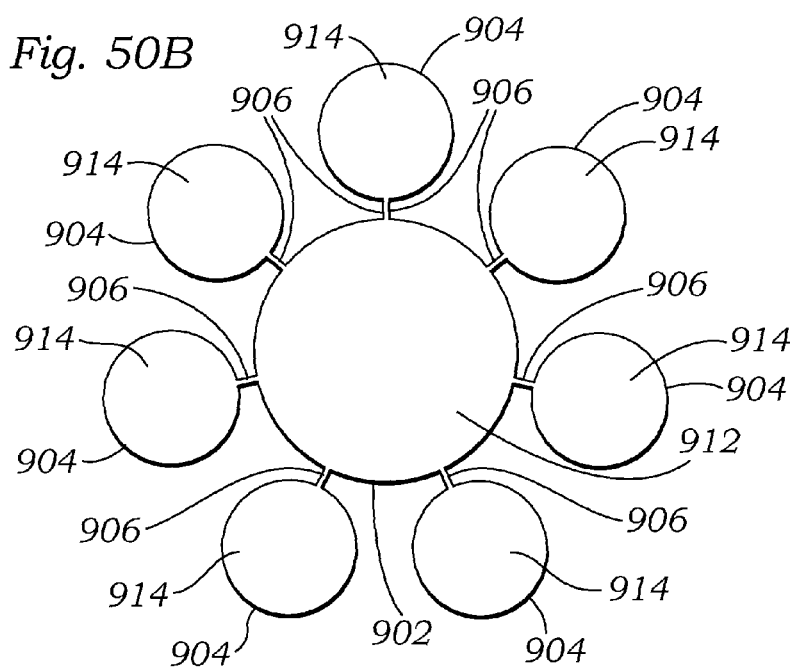
FIG. 50B is a cross-sectional view taken along line 50B-50B of FIG. 49.

FIGS. 49, 50A, and 50B illustrate another embodiment of an expansion device 900. Expansion device 900 comprises an inner balloon member 902 and a plurality of outer balloon members 904. Inner balloon member 902 and outer balloon members 904 can be constructed by fusing portions of a single balloon. Thus, for example, as shown in FIG. 49, a single balloon can be pinched and/or fused along a plurality of lines 906 to provide the plurality of outer balloon members 904.

Because lines 906 do not extend the full length of the expansion device 900, a cross section taken along line 50A-50A reveals only a single lumen 909 at a proximal end 908 of expansion device 900. Similarly, if a cross section were taken near a distal end 910 of expansion device 900 it would also show only a single lumen. As a result of the fusing of portions of expansion device 900 along lines 906, lumen 909 splits into a plurality of lumen between the proximal end 908 and distal end 910 of expansion device 900. The plurality of lumens include a central lumen defined by inner balloon member 902 and a plurality of lumens that are defined by outer balloon members 904. FIG. 50B is a cross-sectional view taken along line 50B-50B in FIG. 49, showing how lumen 909 splits into an inner lumen 912 and a plurality of outer lumen 914. Because all lumen are in fluid communication with one another, when an inflation fluid is delivered into lumen 909, the inflation fluid simultaneously moves into inner lumen 912 and outer lumens 914.

The expansion devices described herein can provide uniform radial expansion of a valve annulus during a valvuloplasty procedure and uniform radial expansion of a prosthetic valve in a valve replacement procedure. Also, it should be note that such expansion devices can be used in stand-alone valvuloplasty procedures, as well as in valvuloplasty procedures performed in preparation of a valve replacement procedure. For example, the expansion device can be used to perform a valvuloplasty procedure and then used to expand a prosthetic device in the same annulus. The expansion devices described herein can allow blood to flow across and/or through the expansion device, which can allow the device to be expanded for a longer duration of time and can reduce the need to pace the heart during a procedure where the expansion device is expanded in an annulus.

The expansion devices described herein can radially expand a prosthetic valve to a shape that is generally circular in cross section by expanding an inner, central expandable member and one or more outer expandable members. Conventional multiple balloon expansion devices are not capable of performing such uniform circular expansion while also providing for sufficient blood perfusion across the expansion member. For example, a three balloon device with the three balloon members positioned side-by-side may provide passageways for blood perfusion, but it will expand to a shape that is tri-lobular in cross section—not circular. The expansion devices described herein are capable of expanding to a shape that is substantially circular in cross section, while allowing sufficient blood to pass through the device. In addition, the sequential or staged expansion of the expansion devices described herein can permit a substantially circular deployment of a prosthetic valve at each stage of deployment.

The methods and apparatuses provided herein also include securement and stabilizing means for securing prosthetic devices during deployment of the prosthetic valve in a native aortic valve annulus. Because of the substantial pressures present in the left ventricle, securement and stabilizing devices, such shown in FIGS. 18A-19C and FIGS. 27-31, can be useful to maintain the prosthetic valve in position on the expansion device.

Although the detailed description generally describes the deployment of a prosthetic valve within the aortic annulus, it should be understood that the expansion devices described herein can be used to expand other prosthetic valves or stents in other areas of the body, including, for example, the delivery of a bare stent in the coronary artery. In addition, the expansion devices described herein can also be used in other medical procedures where an annulus or passageway of the cardiovascular system is to be enlarged, either with or without the deployment of a stent or other prosthetic member. For example, the expansion devices described herein can be used in angioplasty procedures, including for example, coronary artery dilation procedures. However, for the reasons discussed above, the expansion devices described herein are particularly advantageous in valvuloplasty and replacement valve procedures.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for delivering an expandable member through the vasculature of a patient comprising:
    delivering in an unexpanded state an expandable member at a distal end of an elongate shaft to a treatment site, the expandable member having a distal end and a proximal end, the expandable member comprising an inner expandable member and a plurality of outer expandable members at least partially surrounding the inner expandable member, wherein the plurality of outer expandable members are not fixed relative to an outer surface of the inner expandable member at an area between proximal and distal ends of the inner expandable member, and each outer expandable member comprises a main section and at least one substantially narrowed section, the at least one substantially narrowed section distal and/or proximal of the main section, the main section of each outer expandable member extending along in contact with the outer surface of the inner expandable member when the expandable member is in the unexpanded state;
    positioning a prosthetic device in a crimped state on the expandable member;
    expanding the inner expandable member in a passageway of the body of the patient;
    expanding the plurality of outer expandable members in the passageway, wherein expansion of the inner and outer expandable members expands the prosthetic device at the treatment site; and
    permitting blood to pass through a plurality of gaps formed between an inner surface of the passageway and outer surfaces of the inner and outer expandable members.

2. The method of claim 1, wherein positioning the prosthetic device comprises positioning a prosthetic heart valve.

3. The method of claim 1, wherein positioning the prosthetic device on the expandable member comprises repositioning the prosthetic device in the crimped state from a location different from a location of the expandable member onto the expandable member.

4. The method of claim 1, wherein delivering an expandable member to a treatment site comprises advancing the expandable member through a guide catheter.

5. The method of claim 1, wherein delivering the expandable member to a treatment site comprises delivering the expandable member to a heart valve and performing a valvuloplasty.

6. The method of claim 1, wherein expanding the inner expandable member is performed independently of expanding the outer expandable members.

7. The method of claim 1, wherein expanding the outer expandable members comprises expanding one or more of the outer expandable members before expanding the other of the outer expandable members.

8. The method of claim 1, wherein the outer expandable members are coupled to the outer surface of the inner expandable member at a distal end and a proximal end of the inner expandable member.

9. The method of claim 8, wherein the outer expandable members are movable relative to the inner expandable member between the distal and proximal ends of the inner expandable member.

10. A method for deploying a prosthetic heart valve without rapid pacing in a patient in need thereof, the method comprising:
    positioning a prosthetic heart valve in a crimped state on an expansion device of a delivery system, the expansion device disposed at a distal end portion of a balloon catheter, the expansion device comprising:
        an inner expandable member and a plurality of outer expandable members at least partially surrounding the inner expandable member, the plurality of outer expandable members not fixed relative to an outer surface of the inner expandable member between proximal and distal ends of the inner expandable member, each outer expandable member comprising a main section and at least one substantially narrowed section, the at least one substantially narrowed section distal or proximal of the main section, wherein positioning the prosthetic heart valve in the crimped state on the expansion device comprises crimping the prosthetic heart valve at a location of the delivery system other than the expansion device and repositioning the prosthetic heart valve onto the expansion device;

advancing the prosthetic heart valve through the vasculature to a native heart valve;

expanding the inner expandable member;

expanding the outer expandable members, thereby forming a plurality of gaps in the expansion device; and permitting blood flow through a plurality of gaps, thereby deploying the prosthetic heart valve in the native heart valve without rapid pacing.

11. The method of claim 10, wherein advancing the prosthetic heart valve through the vasculature comprises advancing the prosthetic heart valve through a guide catheter.

12. The method of claim 10, wherein the delivery system further comprises a nose cone.

13. The method of claim 10, further comprising repositioning the prosthetic heart valve.

14. The method of claim 10, wherein expanding the inner expandable member is performed independently of expanding the outer expandable members.

15. A method for performing a valvuloplasty without rapid pacing in a patient in need thereof, the method comprising:

positioning an expansion device disposed at a distal end portion of a balloon catheter, the expansion device comprising:

an inner expandable member and a plurality of outer expandable members at least partially surrounding the inner expandable member, the plurality of outer expandable members not fixed relative to an outer surface of the inner expandable member between proximal and distal ends of the inner expandable member, each outer expandable member comprising a main section and at least one substantially narrowed section, the at least one substantially narrowed section distal or proximal of the main section;

advancing the expansion device through the vasculature to a native heart valve;

expanding the inner expandable member;

expanding the outer expandable members, thereby forming a plurality of gaps in the expansion device, wherein expanding the outer expandable members comprises expanding one or more of the outer expandable members before expanding the other of the outer expandable members; and permitting blood flow through a plurality of gaps, thereby performing a valvuloplasty of the native heart valve without rapid pacing.

16. The method of claim 15, wherein expanding the inner expandable member is performed independently of expanding the outer expandable members.

* * * * *